United States Patent
Itoh et al.

(10) Patent No.: US 7,524,549 B2
(45) Date of Patent: *Apr. 28, 2009

(54) METHOD FOR EVALUATING OPTICAL INFORMATION MEDIUM AND OPTICAL INFORMATION MEDIUM

(75) Inventors: Hidetake Itoh, Tokyo (JP); Kazushi Tanaka, Tokyo (JP); Naoki Hayashida, Tokyo (JP); Hiroshi Take, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/856,517

(22) Filed: Sep. 17, 2007

(65) Prior Publication Data

US 2008/0014400 A1    Jan. 17, 2008

Related U.S. Application Data

(60) Division of application No. 11/106,436, filed on Apr. 15, 2005, now Pat. No. 7,338,695, which is a continuation of application No. PCT/JP03/13521, filed on Oct. 23, 2003.

(30) Foreign Application Priority Data

Oct. 30, 2002  (JP) .................. 2002-316766
Oct. 30, 2002  (JP) .................. 2002-316901

(51) Int. Cl.
    *B41M 3/02*    (2006.01)
(52) U.S. Cl. .................. 428/64.4; 369/53.2; 369/53.21; 369/53.41; 430/270.11
(58) Field of Classification Search ............ None
    See application file for complete search history.

(56) References Cited

U.S. PATENT DOCUMENTS

| | | | |
|---|---|---|---|
| 6,924,019 B2 | 8/2005 | Suzawa et al. | |
| 7,338,695 B2 * | 3/2008 | Itoh et al. | 428/64.4 |
| 2004/0234720 A1 | 11/2004 | Hayashida et al. | |
| 2005/0013965 A1 | 1/2005 | Itoh et al. | |
| 2005/0191410 A1 | 9/2005 | Itoh et al. | |
| 2005/0196576 A1 | 9/2005 | Itoh et al. | |
| 2006/0159857 A1 | 7/2006 | Hayashida et al. | |
| 2006/0203242 A1 | 9/2006 | Itoh et al. | |

(Continued)

FOREIGN PATENT DOCUMENTS

EP     0 552 636 A1    7/1993

(Continued)

OTHER PUBLICATIONS

TDK Homepage, http://www.tdk.co.jp/, Oct. 28, 2002.

(Continued)

*Primary Examiner*—Bruce H Hess
(74) *Attorney, Agent, or Firm*—Oblon, Spivak, McClelland, Maier & Neustadt, P.C.

(57) ABSTRACT

An optical information medium includes a light-transmitting supporting substrate, an information recording layer on one surface of the supporting substrate, a protective layer on the information recording layer, and a light-transmitting hard coat layer on an other surface of the supporting substrate. The medium is configured to have a recording/reproducing beam incident into the information recording layer through the hard coat later and the supporting substrate.

6 Claims, 2 Drawing Sheets

U.S. PATENT DOCUMENTS

2007/0105227 A1  5/2007  Hayashida et al.

FOREIGN PATENT DOCUMENTS

| | | |
|---|---|---|
| EP | 1 074 859 A2 | 2/2001 |
| EP | 1 146 510 | 10/2001 |
| EP | 1 947 152 A2 | 7/2008 |
| JP | 4-339333 | 11/1992 |
| JP | 6-44617 | 2/1994 |
| JP | 6-349119 | 12/1994 |
| JP | 07-070555 | 3/1995 |
| JP | 07-254169 | 3/1995 |
| JP | 8-248024 | 9/1996 |
| JP | 9-100111 | 4/1997 |
| JP | 9-212913 | 8/1997 |
| JP | 10-110118 | 4/1998 |
| JP | 10-151409 | 6/1998 |
| JP | 10-302311 | 11/1998 |
| JP | 11-185313 | 7/1999 |
| JP | 11-293159 | 10/1999 |
| JP | 2000-17572 | 1/2000 |
| JP | 2000-82236 | 3/2000 |
| JP | 2001-228302 | 8/2001 |
| JP | 2001-325751 | 11/2001 |
| JP | 2002-157779 | 5/2002 |
| JP | 2002-157784 | 5/2002 |
| JP | 2002-190136 | 7/2002 |
| JP | 2002-230837 | 8/2002 |
| JP | 2003-22571 | 1/2003 |
| JP | 2003-168248 | 6/2003 |
| JP | 2004-35824 | 2/2004 |
| JP | 2004-152418 | 5/2004 |
| JP | 2004-171711 | 6/2004 |
| JP | 2004-171741 | 6/2004 |
| JP | 2004-185772 | 7/2004 |
| WO | 03/021587 | 3/2003 |
| WO | WO 03/029382 A1 | 4/2003 |
| WO | WO 2004/040564 A1 | 5/2004 |

OTHER PUBLICATIONS

Naoki Hayashida, et al. "Functional Hard-Coat for Cartridge-Free DVR Blue", Joint International Symposium on Optical Memory and Optical Data Storage Technical Digest IEEE Catalog 02EX552 ISBN #0-7803-7379-0, Jul. 2002, pp. 12-14.

Naoki Hayashida, et al. "High-Performance Hard Coat for Cartridge-Free Blu-Ray Disc" Japanese Journal of Applied Physics vol. 42, Feb. 2003, pp. 750-753.

Naoki Hayashida, et al. "Anti-fingerprint Property of the Hard-Coat for Cartridge-Free Blu-Ray Dis" Optical Data Storage, May 2003, pp. 18-20.

Naoki Hayashida, et al. "Anti-Fingerpring Property of the Hard-Coat for Cartridge-Free Blu-Ray Disc" Optical Data Storage, vol. 5069, SPIE 0277-786X/03, May 2003, pp. 361-368.

The Association of Powder Process Industry and Engineering, Japan, "Appie Jis Test Powders", Sep. 30, 2003 w/ English translation.

\* cited by examiner

Laser beam

METHOD FOR EVALUATING OPTICAL INFORMATION MEDIUM AND OPTICAL INFORMATION MEDIUM

CROSS-REFERENCE TO RELATED APPLICATIONS

This is a divisional of U.S. application Ser. No. 11/106,436, filed Apr. 15, 2005, which is a continuation of PCT/JP2003/013521, filed Oct. 23, 2003, which was published under PCT Article 21 (2) in Japanese. This application is based upon and claims the benefit of priority from the prior Japanese Patent Application Nos. 2002-316766 filed Oct. 30, 2002, and 2002-316901 filed Oct. 30, 2002. The entire contents of each of these documents are incorporated herein by reference.

TECHNICAL FIELD

The present invention relates to a method for evaluating an optical information medium, and more specifically, to a simple method for evaluating an optical information medium by judging the surface quality of the medium by the use of a novel artificial fingerprint liquid as an evaluation dispersion liquid.

The present invention also relates to an optical information medium such as a reproduction-only optical disk, optical recording disk, magneto-optical recording disk, and the like, and more specifically, to an optical information medium having an excellent anti-staining property of the surface which is on the incident side of recording/reproducing beam.

BACKGROUND ART

When an optical disk such as a reproduction-only optical disk, optical recording disk, magneto-optical recording disk, and the like, is used, the adhesion of stains or fingerprints to the surface thereof is caused on the basis of various stain materials. The adhesion of these stains or fingerprints is unpreferable, and the surface of the optical disk is usually subjected to an appropriate surface treatment in order to improve an anti-staining property thereof, decrease a fingerprint adhering property or improve a fingerprint removing property.

For example, investigations are being made on various water repellent or oil repellent treatments to the surface of the optical disk. In order to check the effect of improving the anti-staining property by the surface treatments, in many cases, there is used a manner of adhering a fingerprint actually onto the optical disk surface and, then, evaluating the wiping-off property thereof with the naked eye. However, such an evaluating manner is poor in quantitativeness and reproducibility.

On the assumption that if the water repellency or the oil repellency of the optical disk surface is high, stain materials are easily removed, the following is frequently performed: measurement of the contact angles of various liquids, such as water and aliphatic hydrocarbons, to the above treated-surface. However, the evaluation based on the contact angle or surface free energy is, in a sense, an indirect evaluating manner. Accordingly, it can be properly used as a manner for evaluating the anti-staining property in only a highly restricted case where the above-mentioned assumption that if the water repellency or the oil repellency is high, excellent anti-staining property is exhibited comes into effect. This evaluating manner gives only a relative evaluation result at best. In other words, when this evaluating manner is applied to an optical disk surface, it is substantially impossible that a threshold value which represents whether or not the disk can be used without causing any practical problem is determined for the contact angle or surface free energy.

In recent years, it has been desired that about optical information media the recording density thereof is made higher in order to store a mass of data such as moving image data. Thus, researches and developments are being actively made for making the density of recording capacity higher. As one of them, the following suggestion is made: as seen in, for example, a DVD, the recording/reproducing wavelength thereof is made short and the numerical aperture (NA) of the objective lens is made large, thereby making the condensed spot diameter of the reproducing/reproducing beam small. As compared with a CD, a recording capacity (4.7 GB/surface) 6 to 8 times that of the CD is actually attained by changing the recording/reproducing wavelength from 780 nm to 650 nm and changing the numerical aperture (NA) from 0.45 to 0.60. Recently, as a method for recording high-quality moving images for a long time, an attempt has been made to make the recording/reproducing wavelength short up to about 400 nm and making the numerical aperture high up to 0.85, so as to attain a recording capacity 4 times or more that of DVD.

However, when the recording density is made high in this way, the condensed spot diameter of the recording/reproducing beam becomes small. Consequently, the recording medium becomes more sensitive to dust, dirt, fingerprints or the like adhering to the laser beam incident side surface of the medium than the conventional art. In particular, about stains containing an organic material, such as fingerprints, a large effect is produced when the stains adhere to the laser beam incident side surface. Since the stains are not easily removed, many countermeasures have been considered so far.

For example, Japanese Laid-open Patent Publication Nos. 10-110118 (1998) and 11-293159 (1999) suggest that when a hard coat agent coated film is formed on a surface of an optical disk substrate made of polycarbonate or the like, a non-crosslinking type fluorine type surfactant is incorporated into the hard coat agent. In order to evaluate the anti-staining property of the hard coat surface of the optical disk, there is performed an operation of adhering an artificial fingerprint liquid wherein a small amount of sodium chloride, urea and lactic acid is dissolved in a mixture solution of water and ethanol onto the surface of the hard coat under pressure, using a pseudo fingerprint, and then determining the wiping-off property thereof with the naked eye. This artificial fingerprint liquid is a liquid described in JIS K2246: 1994 "Rust Preventing Oil". The JIS standard prescribes a performance-testing method for rust preventing oils used for temporary rust-prevention of metal materials such as steel. Accordingly, the artificial fingerprint liquid is prepared to determine the corrosiveness of metal materials. For this reason, the liquid is not useful at all for purposes other than this. Even if the artificial fingerprint liquid made mainly of water and ethanol is adhered onto a surface of an optical disk substrate made of resin such as polycarbonate, in reality the artificial fingerprint liquid is repelled and is not fixed on the substrate surface in almost all cases. It can be considered from this fact that the resin substrate surface exhibits the same wiping-off property against the artificial fingerprint liquid whether the surface is not subjected to any surface treatment or is subjected to surface treatment. That is, it is hardly significant to use the artificial fingerprint liquid prescribed in JIS K2246: 1994 for evaluation of the anti-staining property or the fingerprint removing property of an optical disk surface.

From such an actual situation, it is desired to develop an artificial fingerprint liquid for quantitatively and with a good reproducibility evaluating the surface quality of an optical disk. It is also desired to develop a simple evaluating method for quantitatively and reproducibly judging the surface quality of an optical disk by the use of the artificial fingerprint liquid.

Furthermore, it is desired to develop an optical disk having a surface with an excellent anti-staining property for use in DVD system, which employ recording/reproducing wavelength of 650 nm, as well as an optical disk having a surface with an excellent anti-staining property for the new system, which employ recording/reproducing wavelength of approximately 400 nm.

DISCLOSURE OF THE INVENTION

OBJECTS OF THE INVENTION

Thus, an object of the present invention is to solve the above-mentioned problems of the conventional art and provide a simple method for evaluating an optical information medium by judging quantitatively and reproducibly the surface quality of the optical information medium by the use of a novel artificial fingerprint liquid as an evaluation dispersion liquid.

Furthermore, an object of the present invention is to provide an optical information medium having a remarkably excellent anti-staining property of the surface which is on the incident side of recording/reproducing beam.

SUMMARY OF THE INVENTION

The present invention comprises the following inventions.

(1) A method for evaluating an optical information medium, comprising the steps of:

adhering an evaluation dispersion liquid containing a fine-particle-form substance and a dispersion medium capable of dispersing the fine-particle-form substance onto the surface of the optical information medium which is on the incident side of a recording/reproducing beam;

observing the state of the evaluation dispersion liquid droplets adhered to the medium surface; and judging the quality of the medium surface.

(2) A method for evaluating an optical information medium, comprising the steps of:

adhering an evaluation dispersion liquid containing a fine-particle-form substance and a dispersion medium capable of dispersing the fine-particle-form substance onto the surface of the optical information medium which is on the incident side of a recording/reproducing beam;

measuring an area ratio of the medium surface occupied with the evaluation dispersion liquid droplets adhered per unit area of the medium surface; and judging the quality of the medium surface.

(3) The method for evaluating an optical information medium according to the above (2), wherein the area ratio of the medium surface occupied with the evaluation dispersion liquid droplets having a diameter of 5 µm or larger adhered per unit area of the medium surface is measured, where the diameter is determined by measuring the area of the evaluation dispersion liquid droplet adhered to the medium surface, assuming that each evaluation dispersion liquid droplet is a perfect circle, and calculating the diameter of the perfect circle from the area of the droplet.

(4) The method for evaluating an optical information medium according to the above (2) or (3), wherein the optical information medium is judged as an acceptable medium when the area ratio of the medium surface occupied with the evaluation dispersion liquid droplets adhered per unit area of the medium surface is 25% or less.

(5) A method for evaluating an optical information medium, comprising the steps of:

adhering an evaluation dispersion liquid containing a fine-particle-form substance and a dispersion medium capable of dispersing the fine-particle-form substance onto the surface of the optical information medium which is on the incident side of a recording/reproducing beam;

measuring a diameter of the evaluation dispersion liquid droplets adhered to the medium surface; and judging the quality of the medium surface.

(6) The method for evaluating an optical information medium according to the above (5), wherein the optical information medium is judged as an acceptable medium when the maximum diameter of the evaluation dispersion liquid droplets adhered to the medium surface is 75 µm or less, where the diameter is determined by measuring the area of the evaluation dispersion liquid droplet adhered to the medium surface, assuming that each evaluation dispersion liquid droplet is a perfect circle, and calculating the diameter of the perfect circle from the area of the droplet.

(7) A method for evaluating an optical information medium, comprising the steps of:

adhering an evaluation dispersion liquid containing a fine-particle-form substance and a dispersion medium capable of dispersing the fine-particle-form substance onto the surface of the optical information medium which is on the incident side of a recording/reproducing beam;

measuring the number of the evaluation dispersion liquid droplets adhered per unit area of the medium surface; and judging the quality of the medium surface.

(8) The method for evaluating an optical information medium according to the above (7), wherein the number of the evaluation dispersion liquid droplets having a diameter of 20 µm or larger and 75 µm or less adhered per unit area of the medium surface is measured, where the diameter is determined by measuring the area of the evaluation dispersion liquid droplet adhered to the medium surface, assuming that each evaluation dispersion liquid droplet is a perfect circle, and calculating the diameter of the perfect circle from the area of the droplet.

(9) The method for evaluating an optical information medium according to the above (7) or (8), wherein the optical information medium is judged as an acceptable medium when the number of the evaluation dispersion liquid droplets adhered per 500 µm×500 µm area of the medium surface is 100 or less.

(10) A method for evaluating an optical information medium, comprising the steps of:

adhering an evaluation dispersion liquid containing a fine-particle-form substance and a dispersion medium capable of dispersing the fine-particle-form substance onto the surface of the optical information medium which is on the incident side of a recording/reproducing beam;

measuring a relationship between a perimeter and an area of the evaluation dispersion liquid droplets adhered to the medium surface; and judging the quality of the medium surface.

(11) The method for evaluating an optical information medium according to the above (10), wherein the relationship between the perimeter and the area of the evaluation dispersion liquid droplets having a diameter of 20 µm or larger adhered to the medium surface is measured, where the diameter is determined by measuring the area of the evaluation dispersion liquid droplet adhered to the medium surface, assuming that each evaluation dispersion liquid droplet is a perfect circle, and calculating the diameter of the perfect circle from the area of the droplet.

(12) The method for evaluating an optical information medium according to the above (10) or (11), wherein the optical information medium is judged as an acceptable medium when the perimeter and the area of the evaluation dispersion liquid droplets adhered to the medium surface, in average value, satisfy the following relationship (1):

$$4\pi \times \text{area}/(\text{perimeter})^2 \geqq 0.75 \qquad (1).$$

(13) The method for evaluating an optical information medium according to any one of the above (1) to (12), which is applied to the optical information medium wherein the smallest diameter of the recording/reproducing beam on the surface which is on the incident side of the recording/reproducing beam is 500 μm or less.

The method for evaluating an optical information medium according to any one of the above (1) to (13), wherein the fine-particle-form substance contained in the evaluation dispersion liquid has an average particle size of 0.05 μm or more and 30 μm or less.

The present invention provides a simple method for evaluating an optical information medium such as a reproduction-only optical disk, optical recording disk, magneto-optical recording disk, and the like, by judging quantitatively and reproducibly the quality of the recording/reproducing beam incident side surface of the optical information medium by the use of a novel artificial fingerprint liquid. The present method enables very simple judgment of the quality of the medium surface by observing the state of the artificial fingerprint liquid droplets adhered to the medium surface, without measuring tracking and jitter value of the optical information medium.

The present invention further comprises the following inventions.

(14) An optical information medium, in which when an evaluation dispersion liquid containing a fine-particle-form substance and a dispersion medium capable of dispersing the fine-particle-form substance is adhered onto the surface of the optical information medium which is on the incident side of a recording/reproducing beam, an area ratio of the medium surface occupied with the evaluation dispersion liquid droplets adhered per unit area of the medium surface is 25% or less.

(15) An optical information medium, in which when an evaluation dispersion liquid containing a fine-particle-form substance and a dispersion medium capable of dispersing the fine-particle-form substance is adhered onto the surface of the optical information medium which is on the incident side of a recording/reproducing beam, the maximum diameter of the evaluation dispersion liquid droplets adhered to the medium surface is 75 μm or less, where the diameter is determined by measuring the area of the evaluation dispersion liquid droplet adhered to the medium surface, assuming that each evaluation dispersion liquid droplet is a perfect circle, and calculating the diameter of the perfect circle from the area of the droplet.

(16) An optical information medium, in which when an evaluation dispersion liquid containing a fine-particle-form substance and a dispersion medium capable of dispersing the fine-particle-form substance is adhered onto the surface of the optical information medium which is on the incident side of a recording/reproducing beam, the number of the evaluation dispersion liquid droplets having a diameter of 20 μm or larger and 75 μm or less adhered per 500 μm×500 μm area of the medium surface is 100 or less, where the diameter is determined by measuring the area of the evaluation dispersion liquid droplet adhered to the medium surface, assuming that each evaluation dispersion liquid droplet is a perfect circle, and calculating the diameter of the perfect circle from the area of the droplet.

(17) An optical information medium, in which when an evaluation dispersion liquid containing a fine-particle-form substance and a dispersion medium capable of dispersing the fine-particle-form substance is adhered onto the surface of the optical information medium which is on the incident side of a recording/reproducing beam, the perimeter and the area of the evaluation dispersion liquid droplets having a diameter of 20 μm or larger adhered to the medium surface, in average value, satisfy the following relationship (1):

$$4\pi \times \text{area}/(\text{perimeter})^2 \geqq 0.75 \qquad (1),$$

where the diameter is determined by measuring the area of the evaluation dispersion liquid droplet adhered to the medium surface, assuming that each evaluation dispersion liquid droplet is a perfect circle, and calculating the diameter of the perfect circle from the area of the droplet.

(18) The optical information medium according to any one of the above (14) to (17), which is used in a system wherein the smallest diameter of the recording/reproducing beam on the surface which is on the incident side of the recording/reproducing beam is 500 μm or less.

(19) The optical information medium according to any one of the above (14) to (18), which comprises at least an information recording layer on a supporting substrate, a light-transmitting layer on the information recording layer, and a light-transmitting hard coat layer on the light-transmitting layer, wherein the recording/reproducing beam is incident upon the side of the medium with the hard coat layer.

(20) The optical information medium according to the above (19), wherein the hard coat layer comprises a cured product of a hard coat agent composition containing an active energy ray-curable, silicone-containing compound and/or fluorine-containing compound.

(21) The optical information medium according to the above (19) or (20), further comprising a thin surface layer on the hard coat layer, the thin surface layer comprising a cured product of a composition containing an active energy ray-curable, silicone-containing compound and/or fluorine-containing compound as the major component.

(22) The optical information medium according to any one of the above (19) to (21), wherein the light-transmitting layer and the light-transmitting hard coat layer has a combined thickness of 70 to 150 μm.

(23) The optical information medium according to any one of the above (14) to (22), which is used in a recording/reproducing system using a blue laser beam.

(24) An optical information medium, in which when an evaluation dispersion liquid containing a fine-particle-form substance and a dispersion medium capable of dispersing the fine-particle-form substance is adhered onto the surface of the optical information medium which is on the incident side of a recording/reproducing beam, the maximum diameter of the evaluation dispersion liquid droplets adhered to the medium surface is 300 μm or less, where the diameter is determined by measuring the area of the evaluation dispersion liquid droplet adhered to the medium surface, assuming that each evaluation dispersion liquid droplet is a perfect circle, and calculating the diameter of the perfect circle from the area of the droplet.

(25) The optical information medium according to the above (14) or (24), which is used in a system wherein the smallest diameter of the recording/reproducing beam on the surface which is on the incident side of the recording/reproducing beam is larger than 500 μm.

(26) The optical information medium according to the above (14), (24) or (25), which comprises at least an information recording layer on one surface of a light-transmitting supporting substrate, and a protective layer on the information recording layer, and comprises a light-transmitting hard coat layer on the other surface of the supporting substrate, wherein the recording/reproducing beam is incident upon the side of the medium with the hard coat layer.

(27) The optical information medium according to any one of the above (14) and (24) to (26), which is used in a recording/reproducing system using a blue laser beam.

The present invention provides an optical information medium having a remarkably excellent anti-staining property of the recording/reproducing beam incident side surface. The optical information media of the present invention include an optical information medium in which the smallest diameter of the recording/reproducing beam on the recording/reproducing beam incident side surface is 500 μm or less, and an optical information medium in which the smallest diameter of the recording/reproducing beam on the recording/reproducing beam incident side surface is larger than 500 μm.

MODES FOR CARRYING OUT THE INVENTION

Figure 1:
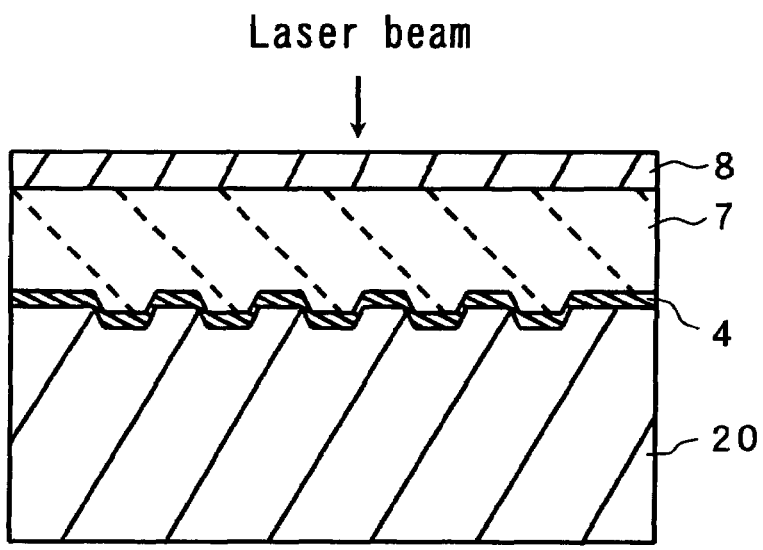
FIG. 1 is a schematic cross-sectional view illustrating a structural example of an optical information medium.

First, a novel artificial fingerprint liquid used as an evaluation dispersion liquid in the present invention is described.

The artificial fingerprint liquid used in the present invention comprises a fine-particle-form substance and a dispersion medium capable of dispersing the fine-particle-form substance. In the present description, the term "dispersion medium" refers only to a liquid component that remains as a pseudo-fingerprint component after the artificial fingerprint liquid has been transferred to the surface of an optical information medium to be evaluated, but not to a diluent that is optionally used when using the artificial fingerprint liquid, and is mostly or completely evaporated finally after the transfer of the artificial fingerprint liquid.

The dispersion medium preferably has a surface tension ranging from 20 to 50 mNm$^{-1}$ at 25° C. By such a constituent, the artificial fingerprint liquid is made up to an artificial fingerprint liquid having a character as close as possible to an actual fingerprint. Thus, the artificial fingerprint liquid can be suitably used for evaluating an anti-staining property, a fingerprint adhering property, or a fingerprint removing property on the surface of various objects.

In the case that an artificial fingerprint liquid of a homogeneous component system made only of a liquid is used at this time, the liquid does not approximate to the removing property of any actual fingerprint. For example, in the case that triolein, which is one of sebum-constituting components, is used as the homogeneous system, the surface tension of triolein is 34 mNm$^{-1}$ at 25° C. Therefore, the surface of polytetrafluoroethylene (PTFE), which has a critical surface tension of about 18 mNm$^{-1}$, repels triolein completely without getting wet. However, actual fingerprints never fail to be fixed even on the PTFE surface. This is mainly because any fingerprint is not made only of a liquid substance but is made of a heterogeneous system containing an insoluble material and a viscous material. Accordingly, by making a heterogeneous system wherein an appropriate insoluble component is added to a dispersion medium made of a liquid component contained in an actual fingerprint and/or a liquid similar thereto, the artificial fingerprint liquid having a character as close as possible to an actual fingerprint can be obtained.

Herein, critical surface tension will be described. The water repellency and the oil repellency of a material can be represented into one way by critical surface tension ($\gamma_c$/mNm$^{-1}$), which is a criterion of the surface free energy of the material. The critical surface tension can be obtained from an actually-measured value of the contact angle thereof. Specifically, the contact angle ($\theta$/rad) to a smooth surface made of a specified material is measured about several saturated hydrocarbon liquids each having a known surface tension (surface tension: $\gamma_1$/mNm$^{-1}$). A value extrapolated to cos $\theta$=1 in plots of cos $\theta$ and $\gamma_1$ is the critical surface tension $\gamma_c$ of the specified material. In order that some material can repel a liquid, it is necessary that the critical surface tension $\gamma_c$ of the material is less than the surface tension $\gamma_1$ of the liquid. For example, $\gamma_c$ of a material having a surface composition of a methylene chain (—CH$_2$—)n is 31 mNm$^{-1}$. Accordingly, the material repels water, which has a surface tension $\gamma_1$ of 73 mNm$^{-1}$ at a temperature of 20° C., but completely gets wet to n-hexadecane, which has a surface tension $\gamma_1$ of 28 mNm$^{-1}$. The contact angle thereof turns to 0 degree.

The artificial fingerprint liquid used in the present invention comprises a fine-particle-form substance in the dispersion medium. The majority of solid components contained in any actual fingerprint is a protein called keratin. In the simplest way, therefore, fine powders of keratin are added to and mixed with the dispersion medium having the above physical property values, so that the above-mentioned artificial fingerprint liquid can be prepared. Indeed, a mixture wherein keratin fine powders are mixed with a dispersion medium, such as water, oleic acid, squalane or triolein, at an appropriate ratio can be effectively used as the artificial fingerprint liquid of the present invention. However, generally available keratin is remarkably expensive. Thus, a large amount thereof cannot be easily obtained. Furthermore, commercially available keratin has a different particle size distribution from that of keratin contained in actual fingerprints. It is therefore necessary to adjust the particle size distribution thereof in advance if necessary. Accordingly, it cannot be necessarily said that the method of using commercially available keratin is a preferable method from the viewpoint of simplicity, measurement precision and its reproducibility.

In order to solve the problems of keratin, the present inventors researched a fine-particle-form substance which can be used instead of keratin. As a result, it has been found that fine particles having a good wettability to the dispersion medium having the above physical property values and having particle sizes close to that of keratin contained in actual fingerprint components are preferable as the fine-particle-form substance.

The artificial fingerprint liquid used in the present invention includes at least one selected from inorganic fine particles and organic fine particles as the fine-particle-form substance. The inorganic fine particles, which are not particularly limited, may be, for example, silica fine particles, alumina fine particles, iron oxide fine particles, and mixtures of any two or more selected from the fine particles. The organic fine particles, which are not particularly limited, may be, for example, keratin fine particles, chitin fine particles, chitosan fine particles, acrylic type fine particles, styrene type fine particles, divinylbenzene type fine particles, polyamide type fine particles, polyimide type fine particles, polyurethane type fine particles, melamine type fine particles, and mixtures of any two or more selected from the fine particles.

All of the inorganic fine particles exhibit, as the constituting component of the artificial fingerprint liquid, the same effect as keratin fine particles, and are further more inexpensive than the keratin fine particles. Therefore, in order to decrease costs and make the performance stable, the content of the inorganic fine particles is preferably 50% by weight or more, more preferably 80% by weight or more, and considerably preferably 100% by weight of the whole of the fine-particle-form substance. It is advisable that organic fine particles such as keratin fine particles may be used together if necessary. Among the organic fine particles, acrylic type fine particles, styrene type fine particles, divinylbenzene type fine particles, polyamide type fine particles, polyimide type fine particles, polyurethane type fine particles, melamine type fine particles and the like are preferable since they are relatively inexpensive.

The fine-particle-form substance preferably has an average particle size (that is, median diameter) of 100 μm or less, and more preferably has an average particle size of 50 μm or less. Examples of the fine-particle-form substance which includes an inorganic component and has an average particle size of 100 μm or less include JIS Z8901 testing powders 1 and 2, ISO testing powder 12103-1, and the Association of Powder Process Industry and Engineering Japan (APPIE) standard powder. All the testing powders are preferable since they have uniform particle sizes and are available at a relatively low cost. Among examples of the JIS Z8901 testing powder 1, Kanto loam is preferable. It is allowable to use, besides the respective testing powders per se, at least one of inorganic fine particles contained in the respective testing powders, for example, at least one selected from various oxide fine particles such as $SiO_2$, $Fe_2O_3$ and $Al_2O_3$. The average particle size of the fine-particle-form substance is preferably 0.05 μm or more, more preferably 0.5 μm or more. Accordingly, the average particle size of the fine-particle-form substance is preferably 0.05 μm or more and 30 μm or less, more preferably 0.5 μm or more and 10 μm or less. If the fine-particle-form substance is too large or too small, the substrate cannot exhibit easily a sufficient function as an alternate material of keratin contained in actual fingerprints.

The fine-particle-form substance preferably has a critical surface tension at 25° C. larger than that of the used dispersion medium at 25° C., and the critical surface tension is preferably 40 mNm$^{-1}$ or more, more preferably 50 mNm$^{-1}$ or more. All of the above particles exemplified as the inorganic fine particles have such a desired nature about the critical surface tension.

In the present invention, as the dispersion medium, there is preferably used a liquid having a surface tension ranging from 20 to 50 mNm$^{-1}$ at 25° C. and a saturated vapor pressure of 760 mmHg (101325 Pa) or less at 200° C. The liquid which constitutes sweat or sebum of human beings or a liquid having a character close to it usually has such physical property values. Accordingly, it is advisable to use a liquid having the physical property values as the dispersion medium of the artificial fingerprint liquid in the present invention. If the surface tension is less than 20 mNm$^{-1}$ at 25° C., the wettability to the surface of an object to be evaluated becomes too high, so that the artificial fingerprint liquid adheres far more easily onto the object surface and is more difficultly removed than actual fingerprints. On the other hand, if the surface tension exceeds 50 mNm$^{-1}$ at 25° C., the wettability to the object surface to be evaluated lowers, so that the artificial fingerprint liquid adheres far more difficultly onto the object surface and is more easily removed than actual fingerprints.

If the saturated vapor pressure exceeds 760 mmHg (101325 Pa) at 200° C., the dispersion medium volatilizes gradually after the adhesion of the fingerprint onto the object surface to be evaluated, so that the state of the adhering artificial fingerprint may change in a short time. What degree of easiness of the volatilization of the dispersion medium is after the adhesion of the fingerprint onto the object surface to be evaluated is also affected by the temperature of the object surface to be evaluated, the temperature of the use environment of the artificial fingerprint liquid, or the like.

In the present invention, it is desirable that the viscosity of the liquid used as the dispersion medium is preferably 500 cP or less, more preferably from 0.5 to 300 cP, and still preferably from 5 to 250 cP at 25° C. By having such a viscosity, the dispersion medium causes the fine-particle-form substance to be satisfactorily dispersed and be easily fixed to the object surface even after the adhesion of the fingerprint onto the object surface to be evaluated.

The dispersion medium is not particularly limited, and examples thereof include higher fatty acid, derivatives of higher fatty acid, terpenes, and derivatives of terpenes. Examples of the higher fatty acid include various acids such as oleic acid, linoleic acid, linolenic acid. The derivatives of higher fatty acid may be ester derivatives, and examples thereof include diglyceride derivatives and triglyceride derivatives (for example, triolein). The terpenes may be various terpenes, and examples thereof include squalane, limonene, α-pinene, β-pinene, camphene, linalool, terpineol, and cadinene. It is advisable to select at least one from these and use the selected one alone or the selected two or more in a mixture form. It is also preferable to mix one or more thereof with water and use the mixture.

In the present invention, an appropriate mixing ratio between the fine-particle-form substance and the dispersion medium depends on the method of adhering the artificial fingerprint liquid onto the object surface to evaluated, which method will be described later, and others. Therefore, the mixing ratio cannot be specified without reservation. In general, however, 0.1 to 5.0 weights of the fine-particle-form substance are preferably added per weight of the dispersion medium, and 0.1 to 3.0 weights of the fine-particle-form substance are more preferably added, and 0.2 to 1.0 weights of the fine-particle-form substance are most preferably added. If the mixing ratio of the fine-particle-form substance to the dispersion medium is too low or too high, it becomes difficult that the resultant functions effectively as an artificial fingerprint liquid. If the fine-particle-form substance is at a ratio less than 0.1, the effect of the addition of the fine-particle-form substance is not obtained, so that the artificial fingerprint liquid is not easily fixed on the object surface to be evaluated or the liquid tends to be easily removed even if the liquid is fixed. On the other hand, if the fine-particle-form substance is added at a ratio over 5.0, liquid crosslinking effect, based on the dispersion medium, on the object surface to evaluated deteriorates, so that the artificial fingerprint liquid tends not to be easily fixed.

As mentioned above, the dispersion medium refers only to a liquid component that remains as a pseudo-fingerprint component after the artificial fingerprint liquid has been transferred to the object surface to be evaluated, but not to a diluent which is described later.

In the present invention, it is also preferable to add a wax, that is, an ester of higher fatty acid and monovalent alcohol to these dispersion medium components, which are liquid at ambient temperature, so as to make the viscosity of the dispersion medium components high. As the wax, for example, the following may be used: a natural wax such as candelilla wax, carnauba wax, urucury wax, rice wax, sugar wax, wood wax, beeswax, spermaceti, Chinese insect wax, shellac wax, or montan wax; or a synthetic wax such as cholesteryl stearate, myristyl myristate, or cetyl palmitate. The addition percentage of each of the waxes may be appropriately determined in accordance with the property of the object to be evaluated, for example, the property of the recording/reproducing optical system of the optical disk, the purpose of the evaluation, and others.

A general thickener may be added to the artificial fingerprint liquid, examples thereof including carrageenan, gum arabic, xanthan gum, galactomannan, and pectin. Furthermore, in order to improve the dispersibility of the fine-particle-form substance, various surfactants may be added, examples thereof including quaternary ammonium salts, alkylbenzenesulfonates, and polyoxyethylene polyoxypropylene glycol.

In the present invention, the artificial fingerprint liquid may be diluted with a diluent such as isopropyl alcohol, methyl ethyl ketone or methoxypropanol if necessary in order to improve the transferring property of the artificial fingerprint. These diluents are mostly or completely evaporated finally after the transfer of the artificial fingerprint liquid to the optical disk surface to be evaluated. The diluent usually has a saturated vapor pressure exceeding 760 mmHg (101325 Pa) at 200° C. It is allowable to add ethanol, liquid paraffin or the like appropriately to the artificial fingerprint liquid.

In a way as described above, the artificial fingerprint liquid used in the present invention is composed. A method is next described for transferring the artificial fingerprint liquid onto the recording/reproducing beam incident side surface of the optical disk to be evaluated to form a pseudo-fingerprint.

In the present invention, when the artificial fingerprint liquid is adhered to the surface of the optical information medium to be evaluated, it is preferable to use a pseudo-fingerprint transferring stamp made of elastomer. Specifically, it is preferable to produce a pseudo-fingerprint transferring stamp made of silicone rubber, butadiene rubber, urethane rubber or the like and use this. The pseudo-fingerprint transferring stamp may be made into such a shape that a fingerprint pattern is precisely copied from a mold which is actually obtained from man's fingers. In a simpler way, it is preferable to use a rubber plug for printing an artificial fingerprint liquid prescribed in JIS K2246-1994. That is, it is possible to use, as the pseudo-fingerprint transferring stamp, a material the surface of which is roughened by polishing a small circular surface (diameter: about 26 mm) of a No. 10 rubber plug with an AA240 abrasive material prescribed in JIS R6251 or JIS R6252 or a abrasive material having performance similar thereto. However, without limitation to the above-mentioned material, a material capable of giving substantially the same pseudo-fingerprint transferring property as described above can be preferably used. In order to obtain a size close to that of an actual fingerprint, an object having a smaller diameter than the above-mentioned rubber plug is preferably used. Specifically, a rubber plug having a diameter of 8 to 25 mm is preferably used, and a rubber plug having a diameter of 8 to 20 mm is more preferably used.

The method of using such a pseudo-fingerprint transferring stamp to transfer the artificial fingerprint liquid, as a pseudo fingerprint, onto an optical disk surface can be appropriately determined in accordance with the purpose of the evaluation. For example, a master plate for pseudo-fingerprint pattern transfer is previously produced, and the rubber plug is used to transfer a pseudo-fingerprint from this master plate onto the optical disk surface. Specifically, the artificial fingerprint liquid is uniformly applied onto a rigid substrate made of glass or resin. As the coating method at this time, an appropriate method may be used from various coating methods such as spin coating and dip coating methods. When the artificial fingerprint liquid is applied onto the substrate, the liquid may be diluted with an appropriate organic solvent such as isopropyl alcohol or methyl ethyl ketone in order to obtain a good application property. It is advisable to evaporate these diluents by air drying or heat drying after the application. In this way, the substrate onto which the artificial fingerprint liquid is uniformly applied is produced and this is used as a master plate for pseudo-fingerprint pattern transfer.

The pseudo-fingerprint transferring stamp is pressed under a predetermined load of 27 N to 35 N against the surface of this master plate onto which the artificial fingerprint liquid is applied, so as to transfer the artificial fingerprint liquid material onto the transferring stamp. Thereafter, the transferring stamp onto which the artificial fingerprint liquid material is transferred is pressed under a predetermined load of 27 N to 35 N against the optical disk surface, so as to transfer the pseudo-fingerprint pattern onto the optical disk surface.

In the present invention, preferred examples of the artificial fingerprint liquid and the transferring method is described below.

The artificial fingerprint liquid is preferably a liquid obtained by: adding a diluent selected from isopropyl alcohol, methyl ethyl ketone and methoxypropanol to a mixture of Kanto loam having an average particle size of 0.5 μm or more and 10 μm or less (JIS Z8901 testing powder) as the fine-particle-form substance and triolein in a weight ratio of Kanto loam to triolein of 0.2 to 1.0.

The transferring stamp is preferably a product obtained by rubbing the circular surface of rubber plug having a diameter of 8 to 20 mm with an AA240 abrasive material prescribed in JIS R6251 or JIS R6252, or with an equivalent abrasive material to make the surface rough.

In a preferred example of the transferring method, the artificial fingerprint liquid is uniformly applied onto a rigid substrate and is then heated to evaporate the diluent, to produce a master plate. Subsequently, a transferring stamp is pressed under a predetermined load of 27 N to 35 N against the surface of the master plate onto which the artificial fingerprint liquid is applied, so as to transfer the artificial fingerprint liquid material onto the transferring stamp. Thereafter, the transferring stamp onto which the artificial fingerprint liquid material is transferred is pressed under a predetermined load of 27 N to 35 N against an optical disk surface, so as to transfer the pseudo-fingerprint pattern onto the optical disk surface.

The use of the above-described method makes it possible that the artificial fingerprint liquid is adhered onto the recording/reproducing beam incident side surface of the optical disk with a good reproducibility.

In the present invention, as described above, the artificial fingerprint liquid is adhered under predetermined conditions onto the recording/reproducing beam incident side surface of the optical disk, and then, the state of the artificial fingerprint liquid droplets adhered to the surface is observed to judge the quality of the medium surface.

Examples of observation of the state of the artificial fingerprint liquid droplets include, for example:
(1) Measurement of the area ratio of the surface occupied with the artificial fingerprint liquid droplets adhered per unit area of the surface;
(2) Measurement of the diameter of the artificial fingerprint liquid droplets adhered to the surface;
(3) Measurement of the number of the artificial fingerprint liquid droplets adhered per unit area of the surface; and
(4) Measurement of the relationship between the perimeter and the area of the artificial fingerprint liquid droplets adhered to the surface (i.e., degree of roundness).

(Measurement of the Area Ratio of the Surface Occupied with the Artificial Fingerprint Liquid Droplets Adhered Per Unit Area of the Surface)

The state of the droplets of the artificial fingerprint liquid adhered to the surface of the optical disk is observed with an optical microscope, and its images are processed on a computer to determine the area ratio of the disk surface occupied with the artificial fingerprint liquid droplets using image-processing technology. Using image-processing technology, the area ratio can be obtained simply by dividing the artificial fingerprint liquid droplets-adhered portion and droplets-free portion into 2-value, measuring respective areas.

Considering the spot size of laser beam, the artificial fingerprint liquid droplets less than 5 µm in diameter adhered to the disk surface are considered to hardly affect the tracking. Therefore, the artificial fingerprint liquid droplets less than 5 µm in diameter may be ignored for the convenience (namely, considered as the artificial fingerprint liquid droplets-free portion) to effect the above measurement. As used herein, "the diameter of the artificial fingerprint liquid droplet" is determined by measuring the area of the artificial fingerprint liquid droplet adhered to the disk surface, assuming that each artificial fingerprint liquid droplet is a perfect circle, and calculating the diameter of the perfect circle from the area of the droplet.

In case of using an artificial fingerprint liquid described in Examples, it has been demonstrated that when the area ratio of the disk surface occupied with the artificial fingerprint liquid droplets exceeds 25%, the tracking fails. Therefore, for evaluation of an optical information medium, the optical information medium in which this area ratio is 25% or less may be judged as an acceptable medium. Further, for safety, the optical information medium in which the area ratio is 20% or less may be judged as an acceptable medium.

(Measurement of the Diameter of the Artificial Fingerprint Liquid Droplets Adhered to the Surface)

In case of using an artificial fingerprint liquid described in Examples, the optical information medium in which the maximum diameter of the artificial fingerprint liquid droplets adhered to the surface is 75 µm or less may be judged as an acceptable medium, in terms of ensuring good tracking.

(Measurement of the Number of the Artificial Fingerprint Liquid Droplets Adhered Per Unit Area of the Surface)

In case of using an artificial fingerprint liquid described in Examples, the number of the artificial fingerprint liquid droplets having a specific diameter of 20 µm or larger and 75 µm or less adhered to the surface may be measured, in terms of ensuring good tracking. Needless to say, in this case, artificial fingerprint liquid droplets having a diameter of larger than 75 µm do not exist. The optical information medium in which the number of the artificial fingerprint liquid droplets adhered per 500 µm×500 µm area of the surface is 100 or less may be judged as an acceptable medium. As can be expected, an optical information medium is favorable if the average diameter of the droplets is small and the number of the droplets is also small.

(Measurement of the Degree of Roundness of the Artificial Fingerprint Liquid Droplets Adhered to the Surface)

It is found that a large distortion in the shape of the artificial fingerprint liquid droplets adhered to the optical disk surface leads to an increase in the diameter of the droplets, as well as the number of the droplets. The distortion of the droplets is caused by the balance between the surface tension of the droplets and the amount of energy required to repel the droplets from the surface of an optical disk (the surface tension of the droplets is a total surface tension including contribution of fine particles, but not the surface tension of the dispersion medium liquid of the artificial fingerprint liquid).

In case of using an artificial fingerprint liquid described in Examples, it has been demonstrated that when the degree of roundness ($=4\pi \times area/(perimeter)^2$) was measured and the average value of the degree of roundness is 0.75 or higher, the diameter and the number of the droplets, as well as the area occupied with the droplets, will fall in a preferred range, and thus, the tracking is well ensured. Therefore, for evaluation of an optical information medium, the optical information medium in which the average value of the degree of roundness is 0.75 or higher may be judged as an acceptable medium. Further, for safety, the optical information medium in which the average value of the degree of roundness is 0.80 or higher, more preferably 0.90 or higher, may be judged as an acceptable medium. Further, the minimum value of the degree of roundness is preferably 0.75 or higher.

Considering the spot size of laser beam, the artificial fingerprint liquid droplets less than 20 µm in diameter adhered to the disk surface are considered to hardly affect the tracking. Therefore, the artificial fingerprint liquid droplets less than 20 µm in diameter may be ignored for the convenience to effect the above measurement.

As described above, the surface quality of the optical information medium can be judged in a simple and accurate manner by measuring any one, or two or more of the following measures:
(1) the area ratio of the surface occupied with the artificial fingerprint liquid droplets;
(2) the diameter of the artificial fingerprint liquid droplets;
(3) the number of the artificial fingerprint liquid droplets; and
(4) the degree of roundness of the artificial fingerprint droplets.

The evaluation method of the present invention is applied to evaluate the surface quality of the optical disk such as a reproduction-only optical disk, optical recording disk, magneto-optical recording disk, and the like, and is preferably applied to the optical information medium in which the smallest diameter of the recording/reproducing beam on the recording/reproducing beam incident side surface is 500 µm or less. In such an optical information medium, if fingerprints or other stains are adhered on the recording/reproducing beam incident side surface of the medium during use of the medium, problem of tracking failure is particularly liable to occur.

Moreover, the evaluation method of the present invention is also applicable to the optical information medium in which the smallest diameter of the recording/reproducing beam on the recording/reproducing beam incident side surface is greater than 500 µm. Likewise, in such an optical information medium, if fingerprints or other stains are adhered on the recording/reproducing beam incident side surface of the medium during use of the medium, problem of tracking failure is liable to occur.

Next is a description of an optical information medium having an excellent anti-staining property of the surface of the present invention, with reference to the drawings (hereinafter, the optical information medium may be referred to as "optical disk"). The above-described evaluation method of the present invention is also applicable to the optical information medium of the present invention.

1. Optical information media in which the smallest diameter of the recording/reproducing beam on the recording/reproducing beam incident side surface is 500 µm or less:

First, an optical information medium in which the smallest diameter of the recording/reproducing beam on the recording/reproducing beam incident side surface is 500 µm or less is described.

A layer structural example of an optical information medium of the present invention is shown in FIG. 1. This optical information medium is a recording medium, and comprises a recording layer (4) that functions as an information recording layer on a supporting substrate (20) of comparatively high rigidity, a light-transmitting layer (7) on the recording layer (4), and a light transmitting hard coat layer (8) on the light-transmitting layer (7). The hard coat layer (8) acts as the surface upon which the recording/reproducing beam is incident, and the laser beam for recording or reproducing is incident through the hard coat layer (8) and the light-transmitting layer (7), and onto the recording layer (4). The thickness of the light-transmitting layer (7), including the hard coat layer (8), is preferably within a range from 30 to 300 µm, and even more preferably from 70 to 150 µm. Such an optical information medium has a hardness of the hard coat layer (8) side of at least grade B in a pencil hardness test.

Although not shown in the drawings, the present invention also includes optical disks with two or more recording layers, in which an additional recording layer is provided on the recording layer (4) with a spacer layer disposed therebetween. In such cases, the light-transmitting layer (7) and the hard coat layer (8) are formed on the recording layer positioned farthest from the supporting substrate (20).

Influence, based on adhesion of a fingerprint, on recording/reproducing property depends on the diameter of a laser beam (the smallest diameter in the case that the beam section is elliptic) on the medium surface which is on the incident side of the laser beam. When this diameter is small, large influences as follows are produced: continuous errors, which cannot be corrected, are made. The present inventors' research has demonstrated that in the case that the diameter of the laser beam incident side surface of the medium is 500 µm or less, in particular, 300 µm or less, bad influence on the recording/reproducing property becomes remarkable when a fingerprint adheres to the medium which is being handled. The diameter of the laser beam, on the laser beam incident side surface of the medium, is represented as follows:

$$2t \cdot \tan\{\sin^{-1}(NA/n)\}$$

wherein the thickness of the light-transmitting layer (7) in FIG. 1 is represented by t, the refractive index of the light-transmitting layer (7) is represented by n, and the numerical aperture of the objective lens of the recording/reproducing optical system is represented by NA.

The present invention can be applied regardless of the kind of the recording layer. That is, the present invention can be applied to a recording medium whether the medium is, for example, a phase-change type recording medium, a bit-forming type recording medium or a magneto-optical recording medium. Usually, a dielectric layer or a reflective layer for protecting the recording layer or attaining an optical effect is laid on at least one side of the recording layer. However, the above laid layer is not shown in FIG. 1. The present invention can be applied to a reproduction-only type, as well as a recordable type as illustrated. In this case, a pit row integrated with the supporting substrate (20) is formed, and a reflective layer (metal layer or dielectric multilayered film) covering the pit row constitutes an information recording layer.

An optical information medium of the present invention that employs a phase-change type recording medium will be described below.

Figure 2:
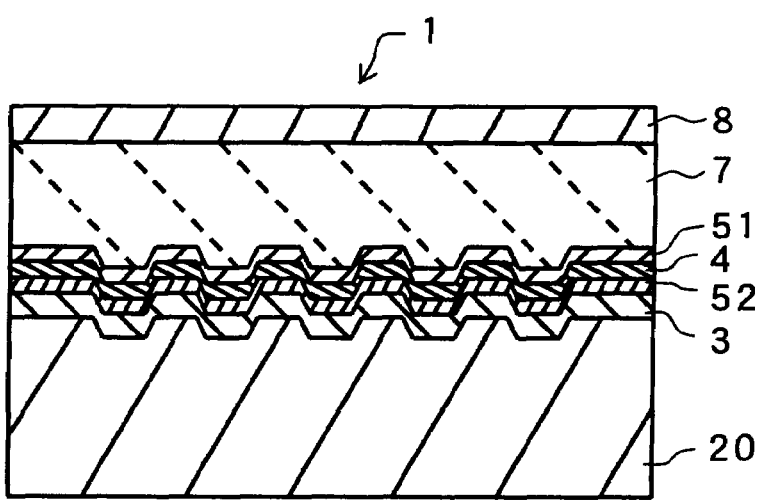
FIG. 2 is a schematic cross-sectional view illustrating another structural example of the optical information medium.

FIG. 2 is a schematic cross-sectional view showing one example of the layer structure of an optical disk of the present invention. In FIG. 2, an optical disk (1) has a supporting substrate (20) having information pits, pregrooves, and other fine scale concavities-convexities formed on one surface thereof. On this surface, the optical disk has a reflective layer (3), a second dielectric layer (52), a phase-change recording material layer (4), and a first dielectric layer (51) formed in this order, and further has a light transmitting layer (7) on the first dielectric layer (51), and a hard coat layer (8) on the light transmitting layer (7). In this example, an information recording layer is formed of the reflective layer (3), the second dielectric layer (52), the phase-change recording material layer (4), and the first dielectric layer (51). When using the optical disk (1), a laser beam for recording or reproducing is incident through the hard coat layer (8) and the light transmitting layer (7).

The supporting substrate (20) has a thickness of 0.3 to 1.6 mm, preferably of 0.5 to 1.3 mm, and includes information pits, pregrooves, and other fine scale concavities-convexities formed on the surface on which the recording layer (4) is formed.

The supporting substrate (20) is not required to be optically transparent when the optical disk is used in such a manner that a laser beam is incident through the light transmitting layer (7) side as described above. However, as transparent materials, various plastic materials including polycarbonate resins, acrylic resins such as polymethyl methacrylate (PMMA), and polyolefine resins and the like may be used. Such flexible materials are particularly useful since the disk warp can be prevented. It should be noted, however, that glass, ceramics or metals and the like may be also used. If a plastic material is employed, the pattern of the concavity-convexity in the surface is often produced by injection molding, whereas the pattern is formed by a photopolymer process (2P process) in the case of any material other than plastics.

The reflective layer (3) is usually deposited by a sputtering process on the supporting substrate (20). As a material for the reflective layer, a metallic element, semi-metallic element, semiconductor element or a compound thereof may be used singly or compositely. More specifically, the material may be selected from known materials for the reflective layers such as Au, Ag, Cu, Al, and Pd. The reflective layer is preferably formed as a thin film with a thickness of 20 to 200 nm.

The second dielectric layer (52), the phase-change recording material layer (4), and the first dielectric layer (51) are deposited in this order by sputtering process on the reflective layer (3), or on the supporting substrate (20) in the case that no reflective layer is provided.

The phase-change recording material layer (4) is formed of a material changing reversibly by irradiation of laser beam between the crystalline state and the amorphous state, and exhibiting different optical properties between these states. Examples of such material include Ge—Sb—Te, In—Sb—

Te, Sn—Se—Te, Ge—Te—Sn, In—Se—Tl, and In—Sb—Te. Further, to any such material, a trace of at least one metal selected from Co, Pt, Pd, Au, Ag, Ir, Nb, Ta, V, W, Ti, Cr, Zr, Bi, In and the like may be added. A trace of reductive gas such as nitrogen also may be added. There is no limitation to the thickness of the recording material layer (4), which is for example in a range of about 3 to 50 nm.

The second dielectric layers (52) and the first dielectric layer (51) are formed on the top and under surfaces of the recording material layer (4), respectively, so as to sandwich the same. The second dielectric layers (52) and the first dielectric layer (51) have not only a function of protecting the recording material layer (4) mechanically and chemically but also a function as an interference layer for adjusting the optical properties. The second dielectric layers (52) and the first dielectric layer (51) may each consist of either a single layer or a plurality of layers.

The second dielectric layers (52) and the first dielectric layer (51) is preferably formed of an oxide, a nitride, a sulfide, or a fluoride or a composite thereof, containing at least one metal selected from Si, Zn, Al, Ta, Ti, Co, Zr, Pb, Ag, Zn, Sn, Ca, Ce, V, Cu, Fe, and Mg. Further, the second dielectric layers (52) and the first dielectric layer (51) preferably have an extinction coefficient k of 0.1 or less.

There is no limitation to the thickness of the second dielectric layer (52), which is preferably for example in a range of about 20 to 150 nm. There is no limitation to the thickness of the first dielectric layer (51), either, which is preferably for example in a range of about 20 to 200 nm. Setting the thicknesses of the second dielectric layers (52) and the first dielectric layer (51) in these ranges makes it possible to adjust reflection.

The light transmitting layer (7) is formed on the first dielectric layer (51) by using active energy ray-curable material, or light-transmitting sheet such as a polycarbonate sheet.

The active energy ray-curable material for the light transmitting layer (7) should be optically transparent, exhibit low optical absorption or reflection in the laser wavelength range to be used, and have low birefringence, and is selected from ultraviolet ray-curable materials, electron ray-curable materials and the like on these conditions.

Specifically, the active energy ray-curable material is constituted preferably of the ultraviolet ray- (electron ray-) curable compound or its composition for polymerization. Examples include monomers, oligomers, polymers and the like in which groups to be crosslinked or polymerized by irradiation with ultraviolet rays, such as acrylic type double bonds such as in ester compounds of acrylate and methacrylate, epoxy acrylates and urethane acrylates, allyl type double bonds such as in diallyl phthalate, and unsaturated double bonds such as in maleic acid derivatives and the like have been contained or introduced into a molecule. These are preferably polyfunctional, particularly trifunctional or more, and may be used alone or in combination thereof. While monofunctional ones may be used for necessary.

The ultraviolet ray-curable monomer is preferably a compound with a molecular weight of less than 2,000, and the oligomer is preferably a compound with a molecular weight of 2,000 to 10,000. These include styrene, ethyl acrylate, ethylene glycol diacrylate, ethylene glycol dimethacrylate, diethylene glycol diacrylate, diethylene glycol methacrylate, 1,6-hexanediol diacrylate, 1,6-hexanediol dimethacrylate etc., and particularly preferable examples include pentaerythritol tetra(meth)acrylate, pentaerythritol tri(meth)acrylate, trimethylolpropane tri(meth)acrylate, trimethylolpropane di(meth)acrylate, (meth)acrylate of phenol ethylene oxide adduct, etc. Besides, the ultraviolet ray-curable oligomer includes oligoester acrylate, acrylic modified urethane elastomer etc.

The active energy ray-curable material may contain known photopolymerization initiators. The photopolymerization initiator is not particularly necessary when electron rays are used as the active energy rays. However, when ultraviolet rays are used, the initiator is necessary. The photopolymerization initiator may be properly selected from the usual photopolymerization initiators such as acetophenone, benzoin, benzophenone, thioxanthone. Examples of a radical photo initiator, among the photopolymerization initiators, include DAROCURE 1173, IRGACURE 651, IRGACURE 184, and IRGACURE 907 (all of which are products manufactured by Ciba Specialty Chemicals Inc.). The content by percentage of the photopolymerization initiator is, for example, from about 0.5 to 5 wt % with respect to the active energy ray-curable component.

As the ultraviolet ray-curable material, a composition containing epoxy resin and a photo-cation polymerization catalyst is also preferably used. The epoxy resin is preferably alicyclic epoxy resin, particularly the resin having 2 or more epoxy groups in the molecule. The alicyclic epoxy resin is preferably one or more of the following compounds: 3,4-epoxycyclohexyl methyl-3,4-epoxycyclohexane carboxylate, bis-(3,4-epoxycyclohexylmethyl)adipate, bis-(3,4-epoxycyclohexyl)adipate, 2-(3,4-epoxycyclohexyl-5,5-spiro-3,4-epoxy)cyclohexane-metha-dioxane, bis(2,3-epoxycyclopentyl)ether and vinyl cyclohexene dioxide etc. Although the epoxy equivalent of alicyclic epoxy resin is not particularly limited, it is preferably 60 to 300, more preferably 100 to 200 for attaining excellent curable properties.

The photo-cation polymerization catalyst used may be any of known ones and is not particularly limited. For example, it is possible to use one or more of the followings: metal fluoroborates and boron trifluoride complexes, bis(perfluoroalkyl sulfonyl)methane metal salts, aryl diazonium compounds, aromatic onium salts of the group 6A elements, aromatic onium salts of the group 5A elements, dicarbonyl chelate of the groups 3A to 5A elements, thiopyrylium salts, the group 6A elements having MF6 anions (M is P, As or Sb), triaryl sulfonium complex salts, aromatic iodonium complex salts, aromatic sulfonium complex salts etc., and it is particularly preferable to use one or more of the followings: polyaryl sulfonium complex salts, aromatic sulfonium salts or iodonium salts of halogen-containing complexions, and aromatic onium salts of the group 3A elements, the group 5A elements and the group 6A elements. The content by percentage of the photo-cation polymerization catalyst is, for example, from about 0.5 to 5 wt % with respect to the active energy ray-curable component.

The active energy ray-curable material used for the light transmitting layer preferably has a viscosity of 1,000 to 10,000 cp (at 25° C.).

In the formation of the light-transmitting layer (7), the application of the active energy ray-curable material onto the surface of the first dielectric layer (51) is preferably conducted using a spin coating method. The cured thickness of the light-transmitting layer (7) may be, for example, about 10 to 300 μm, preferably 20 μm or more and 200 μm or less, particularly 70 μm or more and 150 μm or less, and more particularly 75 μm or more and 150 μm or less. Following application, this curable material can then be cured by irradiation with ultraviolet rays. This ultraviolet-ray irradiation may be divided into a plurality of irradiation doses. Furthermore, the operation of applying the active energy ray-curable material may also be conducted using a plurality of application repetitions, with ultraviolet-ray irradiation conducted after each individual application repetition. By dividing the ultraviolet-ray irradiation operation into a plurality of irradiation doses, the resin is able to be cured in a stepwise manner, thus enabling a reduction in the stress that accumulates in the disk at any one time due to curing shrinkage, leading to a reduction in the overall stress accumulated in the disk. As a result, even if the thickness of the light-transmitting layer (7) is considerably large, as in the case described above, a disk with excellent mechanical characteristics can still be produced.

Alternatively, in the present invention, a light-transmitting layer can also be formed using a light transmitting resin sheet. In such a case, an active energy ray-curable material is applied onto the surface of the first dielectric layer (51), in a similar manner to that described above for formation of a light-transmitting layer, thus forming an uncured resin material layer. A light transmitting sheet is then placed on this uncured resin material layer as the light-transmitting layer (7), and by subsequently irradiating the structure with active energy rays such as ultraviolet rays and curing the underlying resin material layer, the light transmitting sheet is bonded to the structure and forms the light-transmitting layer (7). The active energy ray-curable material of this resin material layer preferably has a viscosity of 3 to 500 cp (at 25° C.). Application of the resin material layer is preferably conducted using a spin coating method. The cured thickness of the resin material layer may be, for example, about 1 to 50 μm.

As the light transmitting sheet, for example, a polycarbonate sheet with any desired thickness within a range from 50 to 300 μm may be used. More specifically, the formation of the light-transmitting layer (7) involves placing the polycarbonate sheet of the desired thickness on the uncured resin material layer under vacuum conditions (0.1 atmospheres or lower), returning the structure to atmospheric pressure, and then conducting irradiation with ultraviolet rays to cure the resin material layer.

A hard coat agent composition which is active energy ray-curable is applied onto the light-transmitting layer (7), and then cured by irradiation with active energy rays such as ultraviolet rays, electron rays or visible rays, thereby forming the hard coat layer (8). The hard coat agent composition preferably comprises:

inorganic fine particles (A) with an average particle size of not more than 100 nm, an active energy ray-curable silicone-containing compound and/or fluorine-containing compound (B), and an active energy ray-curable compound (C) other than the compound (B).

Each component of the hard coat agent composition is described.

The active energy ray-curable compound (C) is different from the silicone-containing compound and/or fluorine-containing compound (B). There are no particular restrictions on the structure of the active energy ray-curable compound (C), provided it is a compound having at least one active group selected from the group consisting of (meth)acryloyl group, vinyl group, and mercapto group. In order to ensure a satisfactory level of hardness for the resulting hard coat, the active energy ray-curable resin preferably comprises a polyfunctional monomers or oligomer containing at least two, preferably at least three polymerizable groups within each molecule. It should be noted that although a high hardness of the hard coat is obtained when the polyfunctional monomers or oligomer are used too much, a large shrinkage in curing causes large warp of the disk.

Among such active energy ray-curable compound, examples of the compound having (meth)acryloyl group include 1,6-hexanediol di(meth)acrylate, triethylene glycol di(meth)acrylate, ethylene oxide modified bisphenol A di(meth)acrylate, trimethylolpropane tri(meth)acrylate, pentaerythritol tetra(meth)acrylate, ditrimethylolpropane tetra (meth)acrylate, dipentaerythritol hexa(meth)acrylate, pentaerythritol tri(meth)acrylate, 3-(meth)acryloyloxyglycerin mono(meth)acrylate, urethane acrylate, epoxy acrylate, and ester acrylate, and the like. However, the compound having (meth)acryloyl group is not limited to these examples.

Examples of the compound having vinyl group include ethylene glycol divinyl ether, pentaerythritol divinyl ether, 1,6-hexanediol divinyl ether, trimethylolpropane divinyl ether, ethylene oxide modified hydroquinone divinyl ether, ethylene oxide modified bisphenol A divinyl ether, pentaerythritol trivinyl ether, dipentaerythritol hexavinyl ether, and ditrimethylolpropane polyvinyl ether, and the like. However, the compound having vinyl group is not limited to these examples.

Examples of the compound having mercapto group include ethylene glycol bis(thioglycolate), ethylene glycol bis(3-mercaptopropionate), trimethylolpropane tris(thioglycolate), trimethylolpropane tris(3-mercaptopropionate), pentaerythritol tetrakis(mercaptoacetate), pentaerythritol tetrakis (thioglycolate), and pentaerythritol tetrakis(3-mercaptopropionate), and the like. However, the compound having mercapto group is not limited to these examples.

As the active energy ray-curable compound (C) contained in the hard coat agent composition, either a single compound or a combination of two or more compounds may be used.

Inorganic fine particles (A) contained in the hard coat agent composition have an average particle size of not more than 100 nm, and preferably not more than 20 nm, in order to ensure good transparency of the hard coat layer. The average particle size of inorganic fine particles (A) is preferably at least 5 nm from the viewpoint of the restrictions associated with producing a colloid solution.

The inorganic fine particles (A) may, for example, be fine particles of metal (or semi-metal) oxides, or fine particles of metal (or a semi-metal) sulfides. Examples of the metals or semi-metals for the inorganic fine particles include Si, Ti, Al, Zn, Zr, In, Sn, and Sb. Aside from the oxides and sulfides, the inorganic fine particles (A) may include selenides, tellurides, nitrides, and carbides. Examples of the inorganic fine particles include fine particles of silica, alumina, zirconia, and titania. Silica fine particles are preferred. When added to the hard coat agent composition, such inorganic fine particles can enhance the abrasion resistance of the hard coat layer.

The silica fine particles are preferably surface-modified with a hydrolyzable silane compound containing active energy ray-reactive groups. Such reactive silica fine particles undergo a crosslinking reaction when exposed to active energy rays during curing of the hard coat and are fixed in the polymer matrix. One example of such reactive silica fine particles is the one described in Japanese Laid-Open Patent Publication No. 9-100111 (1997), which is suitable for use in the present invention.

The active energy ray-curable silicone-containing compound and/or fluorine-containing compound (B) is/are used for imparting water repellency and/or lubricity to the surface of the hard coat layer. Examples of substituent group for imparting water repellency and/or lubricity include silicone-containing substituent group and/or fluorine-containing substituent group. And, examples of the active energy ray-polymerizable reactive group include active energy ray-radical polymerizable reactive groups such as (meth)acryloyl group, vinyl group, and mercapto group; and active energy ray-cationic polymerizable reactive groups such as cyclic ether group, and vinyl ether group. Silicone-containing compound or fluorine-containing compound having said radical polymerizable reactive group or said cationic polymerizable reactive group may be used.

The silicone compounds may include compounds containing a moiety with a silicone-containing substituent and at least one reactive group selected from (meth)acryloyl group, vinyl group, mercapto group, cyclic ether group, and vinyl ether group. Specific examples include, but are not limited to, compounds as represented by the following formulae (1) to (3):

  (1);

  (2); and

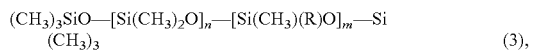  (3), wherein R is a substituent containing at least one reactive group selected from a (meth)acryloyl group, a vinyl group, a mercapto group, a cyclic ether group, and a vinyl ether group n and m represent the degree of polymerization.

Examples of the fluorine-containing compound include a fluorine-containing (meth)acrylate compound. Specific examples of the fluorine-containing (meth)acrylate compound include fluorinated acrylates such as 2,2,3,3,3-pentafluoropropyl (meth)acrylate, 2,2,3,3-tetrafluoropropyl (meth)acrylate, 2,2,2-trifluoroethyl (meth)acrylate, 1H,1H,5H-octafluoropentyl (meth)acrylate, 3-(perfluoro-5-methylhexyl)-2-hydroxypropyl (meth)acrylate, 2-(perfluorooctyl)ethyl acrylate, 3-perfluorooctyl-2-hydroxypropyl (meth)acrylate, 2-(perfluorodecyl)ethyl (meth)acrylate, 2-(perfluoro-9-methyloctyl)ethyl (meth)acrylate, 3-(perfluoro-7-methyloctyl)ethyl (meth)acrylate, 2-(perfluoro-9-methyldecyl)ethyl (meth)acrylate, and 1H,H,9H-hexadecafluorononyl (meth)acrylate. However, the fluorine-containing (meth)acrylate compound is not limited to these examples. For example, it is also preferable to use a polymer compound such as perfluoropolyether into which a (meth)acrylate group is introduced, and a fluorine-containing compound having a vinyl or mercapto group instead of a (meth)acrylate group, or some other compound.

Further, examples of the fluorine-containing compound include those compounds that include a moiety having a fluorine-containing substituent and at least one reactive group selected from cyclic ether group and vinyl ether group. Specific examples include, but are not limited to, 3-(1H,1H-perfluorooctyloxy)-1,2-epoxypropane, 3-(1H,1H-perfluorononyloxy)-1,2-epoxypropane, 3-(1H,1H-perfluorodecyloxy)-1,2-epoxypropane, 3-(1H,1H-perfluoroundecyloxy)-1,2-epoxypropane, 3-(1H,1H-perfluorotetradecyloxy)-1,2-epoxypropane, 3-(1H,1H-perfluorohexadecyloxy)-1,2-epoxypropane, 1H,1H,6H,6H-perfluoro-1,6-hexanediol diglycidylether, 1H,1H,8H,8H-perfluoro-1,8-octanediol diglycidylether, 1H,1H,9H,9H-perfluoro-1,9-nonandiol diglycidylether, 1H,1H,10H,10H-perfluoro-1,10-decanediol diglycidylether, 1H,1H,12H,12H-perfluoro-1,12-dodecanediol diglycidylether, and diglycidylether of Fomblin Z DOL (an alcohol-modified perfluoropolyether (manufactured by Ausimont Co.)). For example, it is also preferable to use compounds in which the reactive group is alicyclic epoxy group, such as 3,4-epoxycyclohexyl group, or vinyl ether group.

In the present invention, the hard coat agent composition preferably comprises:

5% by weight or more and 80% by weight or less of the inorganic fine particles (A), 0.01% by weight or more and 1% by weight or less of the total amount of the silicone-containing compound and/or fluorine-containing compound (B), and 19% by weight or more and 94.99% by weight or less of the active energy ray-curable compound (C), with respect to the total amount of the components (A), (B) and (C).

If more than 80% by weight of the inorganic fine particles (A) is contained, the film strength of the hard coat layer tends to weaken, whereas if the quantity is less than 5% by weight, the effect of improving the abrasion resistance of the hard coat layer is weak.

If more than 1% by weight of the silicone-containing compound and/or fluorine-containing compound (B) is contained, the lubricity of the hard coat layer improves but the hardness of the hard coat layer is likely to be lowered. On the other hand, if the quantity is less than 0.01% by weight, the effect of improving the lubricity is weak.

More Preferably, te Hard Coat Agent Composition Comprises:

10% by weight or more and 60% by weight or less of the inorganic fine particles (A), 0.01% by weight or more and 1% by weight or less of the silicone-containing compound and/or fluorine-containing compound (B), and 39% by weight or more and 89.99% by weight or less of the active energy ray-curable compound (C), with respect to the total amount of the components (A), (B) and (C).

In particular, when 0.025% by weight or more and 0.3% by weight or less of the silicone-containing compound and/or fluorine-containing compound (B) is contained, an optical information medium in accordance with the present invention can be easily obtained. Most preferably, 0.15% by weight or more and 0.25% by weight or less of the silicone-containing compound and/or fluorine-containing compound (B) is contained.

The hard coat agent composition may also comprise above-mentioned known photopolymerization initiators. The photopolymerization initiator is not particularly necessary when electron rays are used as the active energy rays. However, when ultraviolet rays are used, the initiator is necessary. The content of the photopolymerization initiator in the hard coat agent composition is, for example, from about 0.5 to 5% by weight with respect to the total amount of the aforementioned components (A), (B) and (C).

Furthermore, if required, the hard coat agent composition may also comprise a non-polymerizable diluent, an organic filler, a polymerization inhibitor, an antioxidant, an ultraviolet ray absorber, a photo-stabilizer, an antifoamer, a leveling agent, a pigment, a silicon compound, or other additives.

In the present invention, the hard coat agent composition is applied onto the light-transmitting layer (7), thus forming an uncured layer of the hard coat agent composition, and this uncured layer is then irradiated with active energy rays, thereby curing the uncured layer of the hard coat agent composition and forming the hard coat layer (8). The coating method for the application is not limited, and may be any one of various coating methods such as spin coating, dip coating and gravure coating methods. In an alternate method in which a light-transmitting sheet is used to serve as the light-transmitting layer (7), the hard coat layer (8) is first formed onto an elongate raw light-transmitting sheet as described above, and disks are subsequently stamped out from the raw sheet. In the same manner as described above, the disks are placed on the uncured resin material layer and the uncured resin material layer is cured.

When the hard coat agent composition contains the non-reactive organic diluent, the hard coat agent composition is first applied to form an uncured layer of the hard coat agent composition, which is then dried by heating to remove the non-reactive organic solvent. Subsequently, the active energy rays are irradiated to cure the uncured layer of the hard coat agent composition and to thereby form the hard coat layer (8). By first applying the hard coat agent composition using the organic diluent and then removing the organic solvent by heating and drying, the reactive silicone tends to concentrate in the proximity of the surface of the uncured layer of the hard coat agent composition. The result is more silicone existing in the proximity of the surface of the cured hard coat layer (8). This further enhances the lubricity. The heating/drying process is preferably carried out at a temperature of for example 40° C. or more and 100° C. or less. Examples of the non-reactive organic diluent include, but are not limited to, propyleneglycol monomethylether acetate, propyleneglycol monomethylether, ethyleneglycol monomethylether, butyl acetate, methyl ethyl ketone, methyl isobutyl ketone, and isopropyl alcohol. The active energy rays may be properly selected from ultraviolet rays, electron rays, visible rays, and other proper active energy rays. Preferably, ultraviolet rays or electron rays are used. The thickness of the hard coat (8) after curing is adjusted to about 0.5 to 5 μm.

In the present invention, the optical information medium may further comprises on the hard coat layer (8) a thin surface layer which is formed of an applied/cured product of a composition containing an active energy ray-curable, silicone-containing compound and/or fluorine-containing compound as the major component. The thickness of the thin surface layer is, for example, from 1 nm to 100 nm. The thin surface layer serves to further improve the anti-staining property. When such thin surface layer is provided, the active energy ray-curable silicone-containing compound and/or fluorine-containing compound (B) may or may not be contained in the hard coat agent composition for forming the hard coat layer (8).

In this manner described above, a phase-change type optical recording disk as shown in FIG. 2 may be obtained, as the optical information medium in which the smallest diameter of the recording/reproducing beam on the recording/reproducing beam incident side surface is 500 μm or less.

When an artificial fingerprint liquid described in Examples is applied to the optical information medium of the present invention in which the smallest diameter of the recording/reproducing beam on the recording/reproducing beam incident side surface is 500 μm or less, said optical information medium meets the following requirements:

(1) the area ratio of the medium surface occupied with the artificial fingerprint liquid droplets having a diameter of 5 μm or larger adhered per unit area of the medium surface is 25% or less, and preferably 20% or less;
(2) the maximum diameter of the artificial fingerprint liquid droplets is 75 μm or less;
(3) the number of the artificial fingerprint liquid droplets having a diameter of 20 μm or larger and 75 μm or less adhered per 500 μm×500 μm area of the medium surface is 100 or less; and/or
(4) the average value of the degree of roundness of the artificial fingerprint liquid droplets having a diameter of 20 μm or larger adhered to the medium surface is 0.75 or higher, preferably 0.80 or higher, and more preferably 0.90 or higher, and the minimum value of the degree of roundness of the droplets is preferably 0.75 or higher.

Accordingly, the optical information medium of the present invention has an excellent anti-staining property of the surface and ensures good tracking.

2. Optical information media in which the smallest diameter of the recording/reproducing beam on the recording/reproducing beam incident side surface is larger than 500 μm:

Next, an optical information medium in which the smallest diameter of the recording/reproducing beam on the recording/reproducing beam incident side surface is larger than 500 μm is described.

Figure 3:
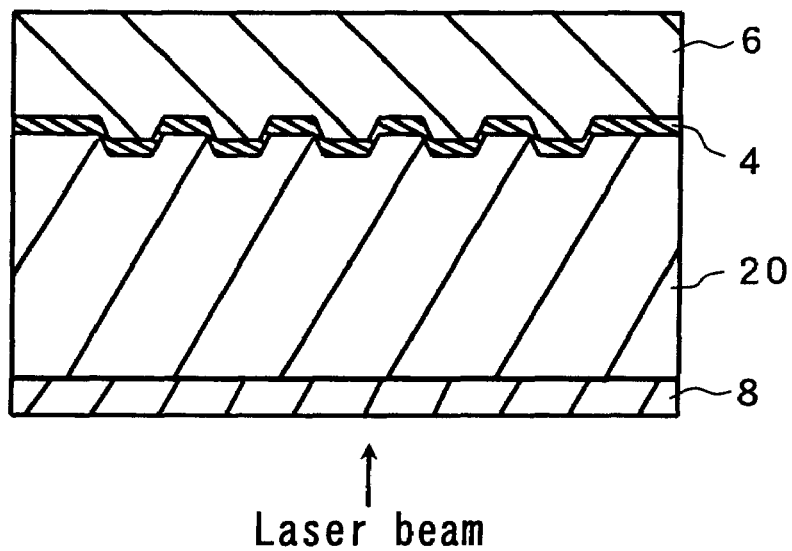
FIG. 3 is a schematic cross-sectional view illustrating a structural example of the optical information medium.

A layer structural example of an optical information medium of the present invention is shown in FIG. 3. The medium shown in FIG. 3 comprises an information recording layer (4) on one surface of a light transmitting supporting substrate (20), and a protective layer (6) on the information recording layer (4), whereas a light transmitting hard coat layer (8) is formed on the other surface of the supporting substrate (20). The hard coat layer (8) acts as the surface upon which the recording/reproducing beam is incident, and the laser beam for recording or reproducing is incident through the hard coat layer (8) and the supporting substrate (20), and onto the recording layer (4).

Figure 4:
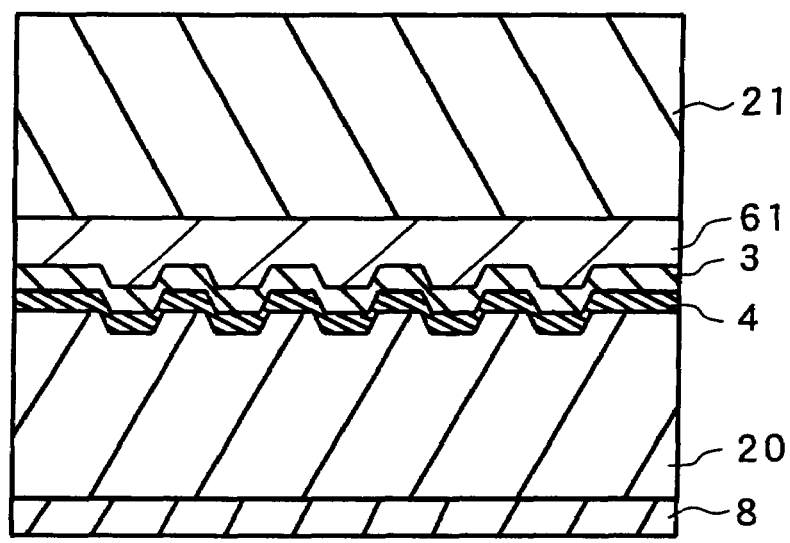
FIG. 4 is a schematic cross-sectional view illustrating another structural example of the optical information medium.

Another layer structural example of an optical information medium of the present invention is shown in FIG. 4. The optical recording medium shown in FIG. 4 comprises an organic dye layer (4) as an information recording layer on one surface of a light transmitting supporting substrate (20), a reflective layer (3) on the dye layer (4), and another supporting substrate (21) that is bonded to the reflective layer (3) via a protective and adhesive layer (61), whereas a light transmitting hard coat layer (8) is formed on the other surface of the supporting substrate (20). The hard coat layer (8) acts as the surface upon which the recording/reproducing beam is incident. In this example, the dye layer (4) and the reflective layer (3) make up the information recording layer. An example of this type of optical disk is the write-once DVD-R format.

In addition to the write-once DVD-R disk shown in FIG. 4, a variety of other disk formats, including read-only DVD-ROM, and rewritable formats such as DVD-RAM and DVD-RW and the like can be commercially available. Read-only DVD formats include DVD-video and DVD-ROM, and with these types of optical disks, concavities-convexities known as pits, which are used to record the information signals, are formed in the surface of the light transmitting supporting substrate during production of the substrate, and a metal reflective layer such as Al, and then a protective layer, are formed sequentially on the supporting substrate. A separate supporting substrate is then bonded to the protective layer via an adhesive layer, thus completing the optical disk. In the case of rewritable DVD formats, the information recording layer may be formed in the same manner as for the phase-change type recording medium described above in the section 1.

The supporting substrate (20) uses a light transmitting base material. Conventionally, the light transmitting supporting substrate (20) is formed by injection molding of a polycarbonate resin, with information formed in the surface of the resin as a series of prepits or pregrooves. However, other materials may also be used, and resins such as polyolefin resins can also be favorably employed. Alternatively, the supporting substrate can also be formed from a flat glass plate, by using the 2P method to form a series of prepits or pregrooves.

A solution of an organic dye dissolved in a solvent is applied onto the surface of the supporting substrate (20) using spin coating, and is then dried to form an organic dye layer (4)

of the desired thickness. The organic dye can be selected from amongst the various cyanine dyes, azo dyes, and phthalocyanine dyes or the like. Techniques other than spin coating, such as spray methods, screen printing methods or vacuum deposition methods can also be used for forming the dye layer, and the thickness of the layer formed can be suitably adjusted in accordance with the dye used.

In those cases where spin coating is used, the dye component is dissolved in a solvent and used in the form of an organic dye solution. The solvent should be a solvent that is capable of satisfactorily dissolving the dye, without having any deleterious effects on the light transmitting base material. The concentration of the dye solution is preferably within a range from 0.01 to 10% by weight.

Specific examples of suitable solvents include alcohol based solvents such as methanol, ethanol, isopropyl alcohol, octafluoropentanol, allyl alcohol, methyl cellosolve, ethyl cellosolve, and tetrafluoropropanol; aliphatic or alicyclic hydrocarbon based solvents such as hexane, heptane, octane, decane, cyclohexane, methylcyclohexane, ethylcyclohexane, and dimethylcyclohexane; aromatic hydrocarbon based solvents such as toluene, xylene, and benzene; halogenated hydrocarbon based solvents such as carbon tetrachloride, chloroform, tetrachloroethane, and dibromoethane; ether based solvents such as diethyl ether, dibutyl ether, diisopropyl ether, and dioxane; ketone based solvents such as 3-hydroxy-3-methyl-2-butanone; ester based solvents such as ethyl acetate and methyl lactate; and water, and of these, a solvent that does not attack the substrate base material should be used. These solvents can either be used singularly, or in combinations of two or more different solvents.

There are no particular restrictions on the thickness of the organic dye layer, although values from about 10 to 300 nm are preferred, and values from about 60 to 250 nm are particularly desirable.

A reflective layer (3) is provided on the organic dye layer (4). The material for the reflective layer must be a material with a satisfactorily high reflectance at the wavelength of the reproducing beam, and suitable examples include metal elements such as Au, Ag, Cu, Al, Ni, Pd, Cr, and Pt, as well as alloys of these metals. Furthermore, the elements listed below may also be included. Namely, metals and semi-metals such as Mg, Se, Hf, V, Nb, Ru, W, Mn, Re, Fe, Co, Rh, Ir, Zn, Cd, Ga, In, Si, Ge, Te, Pb, Po, Sn, and Bi.

The reflective layer can be formed using a sputtering method, ion plating method, chemical deposition method, or vacuum deposition method, although this is not a restrictive list. Furthermore, a conventional inorganic or organic intermediate layer or adhesive layer may be provided between the substrate base material and the reflective layer in order to improve the reflectance and/or improve the recording characteristics of the disk. There are no particular restrictions on the thickness of the reflective layer, although values from about 10 to 300 nm are preferred, and values from about 80 to 200 nm are particularly desirable.

Another supporting substrate (21) is usually bonded to the reflective layer (3) via a protective and adhesive layer (61). This supporting substrate (21) can use the same material as that used for the supporting substrate (20). There are no particular restrictions on the material used for the protective and adhesive layer (61), provided it is capable of bonding the two substrates (21) and (20) together, and protects the reflective layer from external forces. Examples of organic materials include thermoplastic resins, thermosetting resins, ultraviolet ray-curable resins, and the like. Furthermore, examples of inorganic materials include $SiO_2$, $SiN_4$, $MgF_2$, $SnO_2$, and the like. Adhesive layers of thermoplastic resins or thermosetting resins can be formed by dissolving the resin in an appropriate solvent, applying the resin in solution form, and then drying the applied solution. Ultraviolet ray-curable resins can either be applied as is, or dissolved in an appropriate solvent to prepare the solution for application, and then applied the solution, and the applied film is then irradiated with ultraviolet rays to cure the resin and generate the layer. Examples of ultraviolet ray-curable resins include acrylate resins such as urethane acrylate, epoxy acrylate, polyester acrylate, and the like. These materials can be used singularly, or in combinations of two or more materials, and can be formed as either a single layer, or a multilayered film.

Formation of the protective and adhesive layer (61) is conducted using either a application method such as the spin coating method used in forming the recording layer or a casting method, or a different method such as sputtering or chemical deposition.

Furthermore, the adhesive used in the bonding step can use any of a variety of different adhesives, including hot melt adhesives, ultraviolet ray-curable adhesives, heat curable adhesives, and tacky type adhesives, and is applied using a method that is appropriate for the type of adhesive, such as roll coating, screen printing or spin coating, although in the case of DVD-R disks, on the basis of factors such as workability, productivity, and the resulting disk characteristics, an ultraviolet ray-curable adhesive is preferably applied using either a screen printing or spin coating method.

A light transmitting hard coat layer (8) is formed on the other surface of the supporting substrate (20). The material for the hard coat layer (8), and the method used for forming the layer are as described above in the section 1. The hard coat layer (8) acts as the surface upon which the recording/reproducing beam is incident. As the recording/reproducing beam, a laser beam with a wavelength of 650 or 660 nm is used. Further, a blue laser beam can also be used.

In the manner described above, a DVD-R disk as shown in FIG. 4 may be obtained, as the optical information medium in which the smallest diameter of the recording/reproducing beam on the recording/reproducing beam incident side surface is larger than 500 µm.

(Measurement of the Area Ratio of the Surface Occupied with the Artificial Fingerprint Liquid Droplets Adhered Per Unit Area of the Surface)

In the same manner as described above, the area ratio of the surface occupied with the artificial fingerprint liquid droplets is measured.

In case of using an artificial fingerprint liquid described in Examples, it has been demonstrated that when the area ratio of the surface occupied with the artificial fingerprint liquid droplets exceeds 25%, the tracking fails. Therefore, in the optical information medium of the present invention, the area ratio of the medium surface occupied with the artificial fingerprint liquid droplets having a diameter of 5 µm or larger adhered per unit area of the medium surface is 25% or less, and preferably 20% or less.

(Measurement of the Diameter of the Artificial Fingerprint Liquid Droplets Adhered to the Surface)

In case of using an artificial fingerprint liquid described in Examples, it is required that the maximum diameter of the artificial fingerprint liquid droplets adhered to the medium surface is 300 µm or less in order to ensure good tracking. Therefore, in the optical information medium of the present invention, the maximum diameter of the artificial fingerprint liquid droplets is 300 µm or less.

As described above, the optical information medium of the present invention in which the smallest diameter of the recording/reproducing beam on the recording/reproducing beam incident side surface is larger than 500 µm gives a specific value in the measurements of:

(1) the area ratio of the surface occupied with the artificial fingerprint liquid droplets; and
(2) the diameter of the artificial fingerprint liquid droplets.

Accordingly, the optical information medium of the present invention has an excellent anti-staining property of the surface and ensures good tracking.

EXAMPLES

The present invention will be more specifically described by way of the following examples. However, the present invention is not limited to these examples.

1. Examples of optical disks in which the smallest diameter of the recording/reproducing beam on the recording/reproducing beam incident side surface is 500 µm or less:

[Disk Samples]

Six optical recording disk samples No. 1 through No. 6, each having the layered construction as shown in FIG. 2 and having a different surface on the laser beam incident side, were respectively prepared in the following manner.

[Production of Disk Sample No. 1]

Using a disk shaped supporting substrate (20) (formed from polycarbonate, diameter 120 mm, thickness 1.1 mm) in which information recording grooves had been formed, sputtering was used to form a reflective layer (3) of thickness 100 nm comprising $Al_{98}Pd_1Cu_1$ (atomic ratio) on the groove-side surface of the substrate. The depth of the grooves, which is represented by light-path length at a wavelength λ=405 nm, was set into λ/6. The recording track pitch in the groove-recording scheme was set into 0.3 µm.

Subsequently, sputtering with an $Al_2O_3$ target was used to form a second dielectric layer (52) of thickness 20 nm on the surface of the reflective layer (3). Sputtering using an alloy target comprising a phase-changing material was then used to form a recording layer (4) of thickness 12 nm on the surface of the second dielectric layer (52). The composition (atomic ratio) of the recording layer (4) was $Sb_{74}Te_{18}(Ge_7In_1)$. Sputtering with a ZnS (80 mol %)—$SiO_2$ (20 mol %) target was then used to form a first dielectric layer (51) of thickness 130 nm on the surface of the recording layer (4).

Subsequently, a radical polymerizable, ultraviolet ray-curable material with the composition shown below was applied onto the surface of the first dielectric layer (51) by spin coating, and was then irradiated with ultraviolet rays, thus forming a light transmitting layer (7) with a cured thickness of 98 µm.

(Light Transmitting Layer: Composition of the Ultraviolet Ray-curable Material)

| | |
|---|---|
| Urethane acrylate oligomer (Diabeam UK6035, manufactured by Mitsubishi Rayon Co., Ltd.) | 50 parts by weight |
| Isocyanuric acid EO modified triacrylate (Aronix M315, manufactured by Toagosei Co., Ltd.) | 10 parts by weight |
| Isocyanuric acid EO modified diacrylate (Aronix M215, manufactured by Toagosei Co., Ltd.) | 5 parts by weight |
| Tetrahydrofurfuryl acrylate | 25 parts by weight |
| Photopolymerization initiator (1-hydroxycyclohexyl phenyl ketone) | 3 parts by weight |

Further, an ultraviolet ray/electron ray-curable hard coat agent with the composition shown below was applied onto the light transmitting layer (7) by spin coating method to form a coating layer, and the applied coating layer was then heated at 60° C. for 3 minutes in an atmosphere to remove the diluent in the coating layer. And then, the coating layer was irradiated with ultraviolet rays to form the hard coat layer (8) having a thickness of 2 µm. In this manner, the disk sample No. 1 was prepared.

(Composition of the Hard Coat Agent)

Reactive group modified colloidal silica (dispersion medium: propyleneglycolmonomethylether acetate, nonvolatile content:

| | |
|---|---|
| Reactive group modified colloidal silica (dispersion medium: propyleneglycolmonomethylether acetate, nonvolatile content: 40% by weight) | 100 parts by weight |
| Dipentaerythritol hexaacrylate | 48 parts by weight |
| Tetrahydrofurfuryl acrylate | 12 parts by weight |
| Propyleneglycol monomethylether acetate (unreactive diluent) | 40 parts by weight |
| IRGACURE 184 (polymerization initiator) | 5 parts by weight |

[Production of Disk Sample No. 2]

A disk sample No. 2 was prepared in the same manner as in the production of disk sample No. 1, except that the composition of the hard coat agent used in the disk sample No. 1 was altered to the following composition of hard coat agent.

(Composition of Hard Coat Agent)

To 100 parts by weight of the hard coat agent used in the disk sample No. 1, 0.00625 part by weight of bifunctional silicone methacrylate (X-22-164A, manufactured by Shin-Etsu Chemical Co., Ltd., molecular weight: 1,500) was added.

A portion of the bifunctional silicone methacrylate bled out on the surface of the hard coat layer (8), so that the hard coat layer (8) seemed to consist of pseudo two layers.

[Production of Disk Sample No. 3]

A disk sample No. 3 was prepared in the same manner as in the production of disk sample No. 1, except that the composition of the hard coat agent used in the disk sample No. 1 was altered to the following composition of hard coat agent.

(Composition of Hard Coat Agent)

To 100 parts by weight of the hard coat agent used in the disk sample No. 1, 0.0125 part by weight of bifunctional silicone methacrylate (X-22-164A, manufactured by Shin-Etsu Chemical Co., Ltd., molecular weight: 1,500) was added.

[Production of Disk Sample No. 4]

A disk sample No. 4 was prepared in the same manner as in the production of disk sample No. 1, except that the composition of the hard coat agent used in the disk sample No. 1 was altered to the following composition of hard coat agent.

(Composition of Hard Coat Agent)

To 100 parts by weight of the hard coat agent used in the disk sample No. 1, 0.025 part by weight of bifunctional silicone methacrylate (X-22-164A, manufactured by Shin-Etsu Chemical Co., Ltd., molecular weight: 1,500) was added.

[Production of Disk Sample No. 5]

A disk sample No. 5 was prepared in the same manner as in the production of disk sample No. 1, except that the composition of the hard coat agent used in the disk sample No. 1 was altered to the following composition of hard coat agent.

(Composition of Hard Coat Agent)

To 100 parts by weight of the hard coat agent used in the disk sample No. 1, 0.075 part by weight of bifunctional silicone methacrylate (X-22-164A, manufactured by Shin-Etsu Chemical Co., Ltd., molecular weight: 1,500) was added.

[Production of Disk Sample No. 6]

A disk sample No. 6 was prepared in the same manner as in the production of disk sample No. 1, except that the composition of the hard coat agent used in the disk sample No. 1 was altered to the following composition of hard coat agent.

(Composition of Hard Coat Agent)

To 100 parts by weight of the hard coat agent used in the disk sample No. 1, 0.125 part by weight of bifunctional silicone methacrylate (X-22-164A, manufactured by Shin-Etsu Chemical Co., Ltd., molecular weight: 1,500) was added.

[Preparation of Artificial Fingerprint Liquid and Adhesion to the Disk Samples]

0.4 parts by weight of Kanto loam of class 11 testing powder 1 (median diameter: 1.6 to 2.3 μm) prescribed in JIS Z8901 as the fine-particle-form substance, 1 part by weight of triolein as the dispersion medium, and 10 parts by weight of methoxypropanol as the diluent were mixed and stirred to form an artificial fingerprint liquid.

(Formation of Master Plate for Transferring Pseudo-fingerprint Patterns)

A master plate for transferring pseudo-fingerprint patterns was produced as follows. While the artificial fingerprint liquid was sufficiently stirred with a magnetic stirrer, an approximately 1 mL portion of the liquid was collected. The collected liquid was applied onto a polycarbonate substrate (diameter: 120 mm, thickness: 1.2 mm) by spin coating. This substrate was heated at 60° C. for 3 minutes to completely remove methoxypropanol, which was the diluent which had become unnecessary. In this way, master plate for transferring pseudo-fingerprint patterns was obtained.

(Transfer of Pseudo-fingerprint Patterns to the Surface of Disk Samples)

A No. 1 silicone rubber plug was uniformly rubbed with a #240 abrasive paper (having the equivalent performance to AA240 abrasive paper described in the above JIS) on its smaller end surface (diameter: 12 mm) and was used as the pseudo-fingerprint transferring stamp. The rubbed end surface of the pseudo-fingerprint transferring stamp was pressed against the master plate with a load of 29 N for 10 seconds to transfer the artificial fingerprint liquid material to the end surface of the transferring stamp. Subsequently, the end surface of the transferring stamp, onto which the artificial fingerprint liquid material adhered, was pressed against an area of the surface of the hard coat layer 8 of the disk sample No. 1, the area being located about 40 mm apart in the radius direction from the center the disk, with a load of 29 N for 10 seconds to transfer the artificial fingerprint liquid material. In the same manner, the artificial fingerprint liquid material was transferred to each of the disk samples No. 2 through 6.

[Observation of Droplets of the Artificial Fingerprint Liquid on the Surface of the Disk Samples]

The droplets of the artificial fingerprint liquid adhered to the surface of each of the disk samples were observed for various indices to judge the quality of the surface.

(Measurement of the Area Ratio of the Surface Occupied with the Artificial Fingerprint Liquid Droplets Adhered Per Unit Area of the Surface)

The state of the droplets of the artificial fingerprint liquid adhered to the surface of each disk sample was observed with an optical microscope (VK-8510, manufactured by Keyence Co., Ltd.). This image was printed on a printer (VH-P40, manufactured by Keyence Co., Ltd.). And the image was read and was processed on a computer to exclude the artificial fingerprint liquid droplets less than 5 μm in diameter, and to determine the area ratio of the surface area occupied with the artificial fingerprint liquid droplets 5 μm or larger in diameter to the whole surface area, by using an image-processing/analysis software Win ROOF (owned by UBE Scientific Analysis Laboratory, Inc.). As used herein, the diameter of the artificial fingerprint liquid droplet is determined by measuring the area of the artificial fingerprint liquid droplet, assuming that each artificial fingerprint liquid droplet is a perfect circle, and calculating the diameter of the perfect circle from the area of the droplet.

(Measurement of the Diameter of the Artificial Fingerprint Liquid Droplets Adhered to the Surface)

Similarly, the maximum diameter of the droplets of the artificial fingerprint liquid was determined by using the image-processing/analysis software Win ROOF.

(Measurement of the Number of the Artificial Fingerprint Liquid Droplets Adhered Per Unit Area of the Surface)

Similarly, by using the image-processing/analysis software Win ROOF, the artificial fingerprint liquid droplets less than 20 μm in diameter were excluded, and the number of the artificial fingerprint liquid droplets 20 μm or larger in diameter per 500 μm×500 μm area was determined. In the disk sample No. 1, plural droplets of the artificial fingerprint liquid larger than 75 μm in diameter were observed and were in the form of being connected to one another. In the disk sample No. 2, a single droplet of the artificial fingerprint liquid larger than 75 μm in diameter was observed. For the other disk samples, no droplets of the artificial fingerprint liquid larger than 75 μm in diameter were found.

(Measurement of the Degree of Roundness of the Artificial Fingerprint Liquid Droplets Adhered to the Surface)

Similarly, by using the image-processing/analysis software Win ROOF, the artificial fingerprint liquid droplets less than 20 μm in diameter were excluded, and the degree of roundness [$4\pi \times area/(perimeter)^2$] was determined for the artificial fingerprint liquid droplets 20 μm or larger in diameter.

(Correlation Between the Results of the Measurements and Tracking of the Disk Samples)

The results of the measurements for each of the disk samples No. 1 through No. 6 were shown in Table 1 below.

TABLE 1

Results of disk sample measurement

| | No. 1 | No. 2 | No. 3 | No. 4 | No. 5 | No. 6 |
|---|---|---|---|---|---|---|
| Area ratio (%) | 58.0 | 26.0 | 19.0 | 15.0 | 11.0 | 11.0 |
| Maximum diameter (μm) | — | 117 | 62.5 | 67.5 | 47.5 | 52.5 |
| Number of droplets | 38 | 120 | 99 | 75 | 65 | 62 |
| Degree of roundness (average) | — | 0.65 | 0.85 | 0.80 | 0.96 | 0.96 |
| Degree of roundness (minimum) | — | 0.15 | 0.39 | 0.21 | 0.82 | 0.77 |

Using an evaluation apparatus for optical recording media (DDU-1000, manufactured by Pulstec Industrial Co., Ltd.), each of the disk samples No. 1 through No. 6 was subjected to focusing at wavelength $\lambda$=405 nm and NA=0.85, and then to tracking. Good tracking was observed in four of the disk samples No. 3 through No. 6, each of which is in accordance with the present invention.

In the disk sample No. 1, the area ratio of approximately 60% of the disk surface was occupied with the artificial fingerprint liquid droplets, resulting in a failure of the tracking. In the disk sample No. 2, the area ratio occupied with artificial fingerprint liquid droplets was 26% and the maximum diameter of the artificial fingerprint liquid droplets was 117 µm, leading to improper tracking.

As set forth, a significant correlation was found between the results of the measurements according to the present invention and the tracking of the disk samples. This indicates that the evaluation method of the present invention offers a very simple way to judge the quality of the disk surface.

2. Examples of optical disks in which the smallest diameter of the recording/reproducing beam on the recording/reproducing beam incident side surface is larger than 500 µm:

[Disk Samples]

Six DVD-R disk samples No. 7 through No. 10, each having the layered construction as shown in FIG. 4 and having a different surface on the laser beam incident side, were respectively prepared in the following manner.

[Production of Disk Sample No. 7]

An azo dye represented by the following formula was applied by the spin coating method onto one surface of a polycarbonate substrate (20) with a diameter of 120 mm and a thickness of 0.6 mm and having grooves and lands (track pitch (groove pitch)=approx. 0.74 µm) formed on the substrate surface, and dried to form an organic dye layer (4) having a thickness of approximately 100 nm in the groove portion. An Ag alloy reflective layer (3) having a thickness of approximately 110 nm was formed by sputtering method on the organic dye layer (4). Further, a protective layer of ultraviolet ray-curable acrylic resin "DIACURE CLEAR SD318" (manufactured by DaiNippon Ink & Chemicals Inc.) was formed on the reflective layer (3).

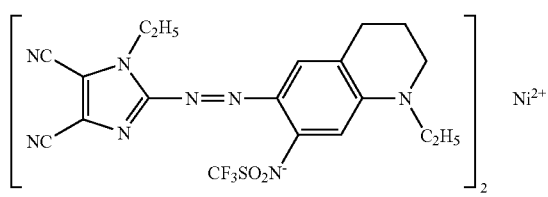

Meanwhile, another polycarbonate substrate (21) with a diameter of 120 mm and a thickness of 0.6 mm and having neither grooves nor lands on the substrate surface was prepared. And the two disks were adhered together by a delayed action cationic polymerizable adhesive "SK7000" (manufactured by Sony Chemicals Corp.) with the protective layer positioned inside. In FIG. 4, the protective layer and the adhesive are together denoted by reference numeral (61) for convenience. The resulting disk was assigned as a disk sample No. 7. The hard coat layer (8) was not formed in the disk sample No. 7.

[Production of Disk Sample No. 8]

An ultraviolet ray/electron ray-curable hard coat agent with the composition shown below was applied onto the other surface of the polycarbonate substrate (20) of the disk sample No. 7 by spin coating method to form a coating layer, and the applied coating layer was then heated at 60° C. for 3 minutes in an atmosphere to remove the diluent in the coating layer. And then, the coating layer was irradiated with ultraviolet rays to form the hard coat layer (8) having a thickness of 2.5 µm.

(Composition of the Hard Coat Agent)

Reactive group modified colloidal silica (dispersion medium: propyleneglycolmonomethylether acetate, nonvolatile content:

| | |
|---|---|
| Reactive group modified colloidal silica (dispersion medium: propyleneglycolmonomethylether acetate, nonvolatile content: 40% by weight) | 100 parts by weight |
| Dipentaerythritol hexaacrylate | 48 parts by weight |
| Tetrahydrofurfuryl acrylate | 12 parts by weight |
| Propyleneglycol monomethylether acetate (unreactive diluent) | 40 parts by weight |
| IRGACURE 184 (polymerization initiator) | 5 parts by weight |

To 100 parts by weight of the mixture of the above-listed components, 0.0015 part by weight of bifunctional silicone methacrylate (X-22-164A, manufactured by Shin-Etsu Chemical Co., Ltd., molecular weight: 1,500) was added to make a hard coat agent. In this manner, a disk sample No. 8 was prepared.

[Production of Disk Sample No. 9]

A disk sample No. 9 was prepared in the same manner as in the production of disk sample No. 8, except that the composition of the hard coat agent used in the disk sample No. 8 was altered to the following composition of hard coat agent.

(Composition of Hard Coat Agent)

To 100 parts by weight of the hard coat agent used in the disk sample No. 8, 0.0025 part by weight of bifunctional silicone methacrylate (X-22-164A, manufactured by Shin-Etsu Chemical Co., Ltd., molecular weight: 1,500) was added.

[Production of Disk Sample No. 10]

A disk sample No. 10 was prepared in the same manner as in the production of disk sample No. 8, except that the composition of the hard coat agent used in the disk sample No. 8 was altered to the following composition of hard coat agent.

(Composition of Hard Coat Agent)

To 100 parts by weight of the hard coat agent used in the disk sample No. 8, 0.02 part by weight of bifunctional silicone methacrylate (X-22-164A, manufactured by Shin-Etsu Chemical Co., Ltd., molecular weight: 1,500) was added.

[Preparation of Artificial Fingerprint Liquid and Adhesion to the Disk Samples]

The same artificial fingerprint liquid as that used in the disk samples No. 1 through No. 6 was used. The artificial fingerprint liquid was transferred to the hard coat (8) surface of each of the disk samples No. 7 through No. 10 (in the disk sample No. 7, the liquid was transferred to the polycarbonate substrate (20) surface) in the same manner as in the disk samples No. 1 through No. 6.

[Observation of Droplets of the Artificial Fingerprint Liquid on the Surface of the Disk Samples]

The droplets of the artificial fingerprint liquid adhered to the surface of each of the disk samples were observed for various indices to judge the quality of the surface.

(Measurement of the Area Ratio of the Surface Occupied with the Artificial Fingerprint Liquid Droplets Adhered Per Unit Area of the Surface)

The state of the droplets of the artificial fingerprint liquid adhered to the surface of each disk sample was observed with an optical microscope (VK-8510, manufactured by Keyence Co., Ltd.). This image was printed on a printer (VH-P40, manufactured by Keyence Co., Ltd.). And the image was read and was processed on a computer to exclude the artificial fingerprint liquid droplets less than 5 μm in diameter, and to determine the area ratio of the surface area occupied with the artificial fingerprint liquid droplets 5 μm or larger in diameter to the whole surface area, by using an image-processing/analysis software Win ROOF (owned by UBE Scientific Analysis Laboratory, Inc.). As used herein, the diameter of the artificial fingerprint liquid droplet is determined by measuring the area of the artificial fingerprint liquid droplet, assuming that each artificial fingerprint liquid droplet is a perfect circle, and calculating the diameter of the perfect circle from the area of the droplet.

(Measurement of the Diameter of the Artificial Fingerprint Liquid Droplets Adhered to the Surface)

Similarly, the maximum diameter of the droplets of the artificial fingerprint liquid was determined by using the image-processing/analysis software Win ROOF.

(Correlation Between the Results of the Measurements and Tracking of the Disk Samples)

The results of the measurements for each of the disk samples No. 7 through No. 10 were shown in Table 2 below.

TABLE 2

| Results of disk sample measurement | | | | |
|---|---|---|---|---|
| | No. 7 | No. 8 | No. 9 | No. 10 |
| Area ratio (%) | 60.0 | 23.0 | 18.0 | 5.0 |
| Maximum diameter (μm) | — | 280 | 220 | 70 |

Using an evaluation apparatus for optical recording media (DDU-1000, manufactured by Pulstec Industrial Co., Ltd.), each of the disk samples No. 7 through No. 10 was subjected to focusing at wavelength $\lambda=650$ nm and NA=0.60, and then to tracking. Good tracking was observed in three of the disk samples No. 8 through No. 10, each of which is in accordance with the present invention.

In the disk sample No. 7, the area ratio of approximately 60% of the disk surface was occupied with the artificial fingerprint liquid droplets, resulting in a failure of the tracking. In this sample, the artificial fingerprint liquid droplets were large and were present in the form of being connected to one another, making it impossible to determine the maximum diameter.

The invention claimed is:

1. An optical information medium comprising:
a light-transmitting supporting substrate;
an information recording layer on one surface of the supporting substrate;
a protective layer on the information recording layer; and
a light-transmitting hard coat layer on an other surface of the supporting substrate,
wherein the medium is configured to have a recording/reproducing beam incident into the information recording layer through the hard coat layer and the supporting substrate, and
a surface of the medium which is on a side on which the recording/reproducing beam is incident is configured such that when an evaluation dispersion liquid containing a fine-particle-form substance and a dispersion medium capable of dispersing the fine-particle-form substance is adhered onto the surface of the medium, a structure of the surface of the medium interacts with the evaluation dispersion liquid such that the maximum diameter of the evaluation dispersion liquid droplets adhered to the medium surface is 300 μm or less, where the diameter is determined by measuring the area of the evaluation dispersion liquid droplet adhered to the medium surface, assuming that each evaluation dispersion liquid droplet is a perfect circle, and calculating the diameter of the perfect circle from the area of the droplet.

2. The optical information medium according to claim 1, which is used in a system wherein the smallest diameter of the recording/reproducing beam on the surface which is on the incident side of the recording/reproducing beam is larger than 500 μm.

3. The optical information medium according to claim 1, which is used in a recording/reproducing system using a blue laser beam.

4. An optical information medium comprising:
a light-transmitting supporting substrate;
an information recording layer on one surface of the supporting substrate;
a protective layer on the information recording layer; and
a light-transmitting hard coat layer on an other surface of the supporting substrate,
wherein the medium is configured to have a recording/reproducing beam incident into the information recording layer through the hard coat layer and the supporting substrate, and
a surface of the medium which is on a side on which the recording/reproducing beam is incident is configured such that, in which when an evaluation dispersion liquid containing a fine-particle-form substance and a dispersion medium capable of dispersing the fine-particle-form substance is adhered onto the surface of the medium, a structure of the surface of the medium interacts with the evaluation dispersion liquid such that an area ratio of the medium surface occupied with the evaluation dispersion liquid droplets adhered per unit area of the medium surface is 25% or less.

5. The optical information medium according to claim 4, which is used in a system wherein the smallest diameter of the recording/reproducing beam on the surface which is on the incident side of the recording/reproducing beam is larger than 500 μm.

6. The optical information medium according to claim 4, which is used in a recording/reproducing system using a blue laser beam.

* * * * *